United States Patent [19]

Takashiki et al.

[11] Patent Number: 5,250,432
[45] Date of Patent: Oct. 5, 1993

[54] METHOD OF CULTURING ANIMAL CELLS

[75] Inventors: Michiyuki Takashiki, Hachioji; Kimihiko Hamamoto, Hino; Kenji Ishimaru, Iwakuni, all of Japan

[73] Assignee: Teijin Limited, Osaka, Japan

[21] Appl. No.: 589,495

[22] Filed: Sep. 27, 1990

Related U.S. Application Data

[63] Continuation-in-part of Ser. No. 463,997, Jan. 12, 1990, abandoned, which is a continuation-in-part of Ser. No. 939,102, Dec. 8, 1986, abandoned.

Foreign Application Priority Data

Dec. 6, 1985 [JP] Japan .................. 60-273503
Apr. 24, 1989 [JP] Japan .................. 1-101641
Jul. 3, 1989 [JP] Japan .................. 1-171393
Sep. 27, 1989 [JP] Japan .................. 1-249269

[51] Int. Cl.$^5$ .......... C12N 5/02; C12N 5/06; C12N 5/12; C12N 5/16
[52] U.S. Cl. .......... 435/240.25; 435/240.26; 435/240.2; 435/813; 435/240.27
[58] Field of Search ............ 435/240.1, 240.2, 240.25, 435/172.2, 2, 240.26, 240.27, 284, 286, 287, 293, 294, 312, 313, 316, 800, 803, 813; 935/108, 109

[56] References Cited

U.S. PATENT DOCUMENTS 4,673,650  6/1987  Braden .................. 435/286
4,900,669  2/1990  Hatch et al. .......... 435/108

FOREIGN PATENT DOCUMENTS 521867   5/1982   Australia .
0164813  12/1985  European Pat. Off. .
0229289  7/1987   European Pat. Off. .
2513264  3/1983   France .
253466   11/1948  Switzerland .
873494   7/1961   United Kingdom .
8201563  5/1982   World Int. Prop. O. .

OTHER PUBLICATIONS

Le Rumeur et al, "Albumin Section and Protein Synthesis by Cultured Diploid and Tetraploid Rat Hepatocytes Separated by Elutriation" Exp. Cell Res. V. 147 247-254, 1983.

Arkhiopv, "Cultivation of Cells on liquid fluorocarbon substrates" Chem. Abstracts, vol. 96, #100292 p. 359, 1982.

Patent Abstracts of Japan, 13(42) (C-564) [3390] (Jan. 30, 1989).

*Primary Examiner*—George C. Elliott
*Attorney, Agent, or Firm*—Wenderoth, Lind & Ponack

[57] ABSTRACT

A method of culturing animal cells, which comprises (A) subjecting living animal cells to suspension culture in a culture tank, (B) withdrawing a portion of a suspension culture fluid containing the living animal cells from the culture tank, (C) supplying the withdrawn suspension culture fluid to a centrifugal separating device which is operated under specific conditions and separating the living animal cells from the suspension culture fluid, (D) withdrawing the separated living animal cells from the centrifugal separating device, and (E) recycling at least a portion of the withdrawn living animal cells to the culture tank for the step (A).

27 Claims, 7 Drawing Sheets

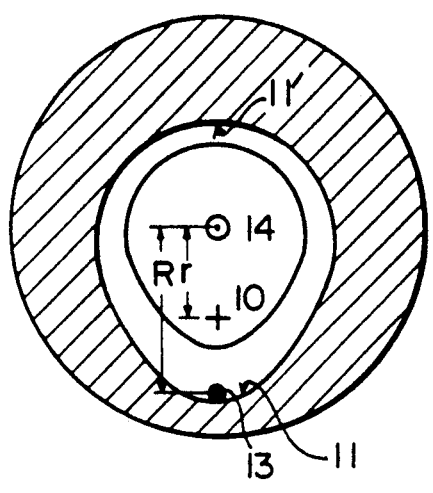 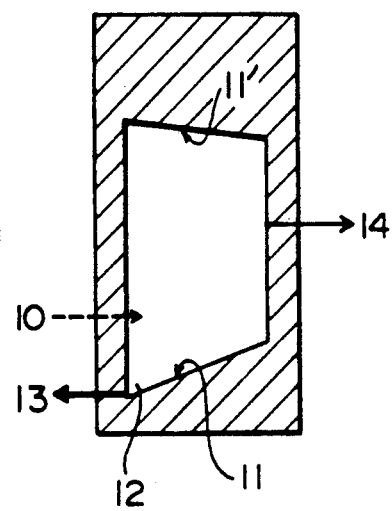
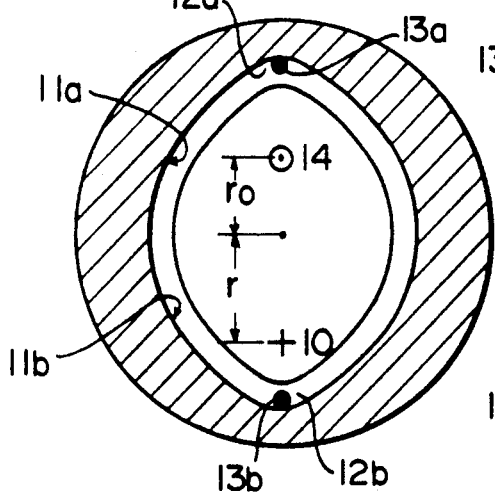 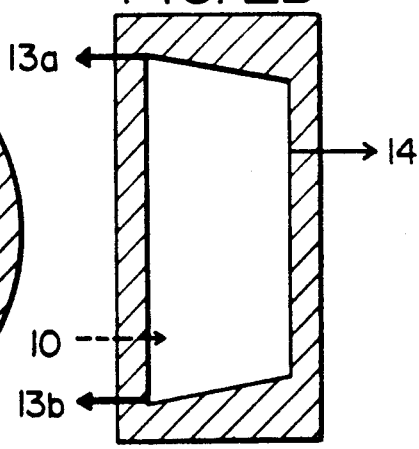
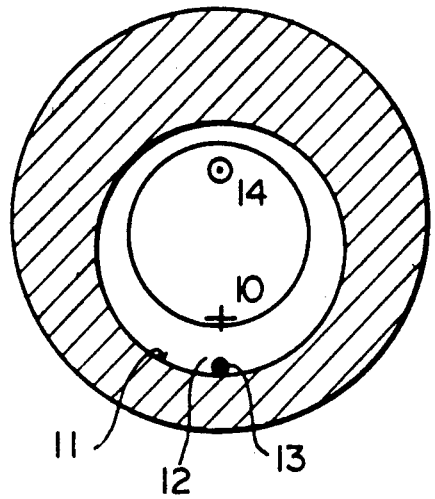 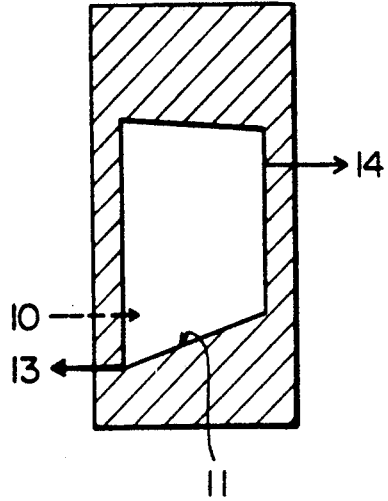

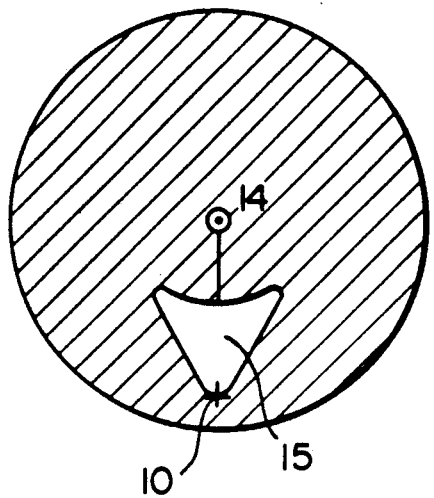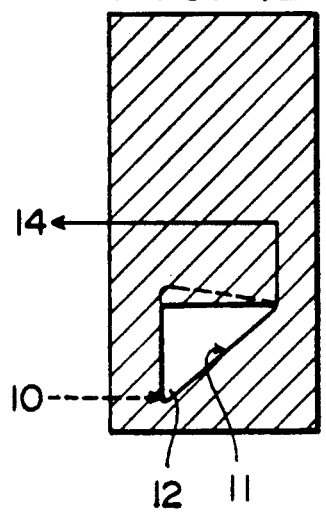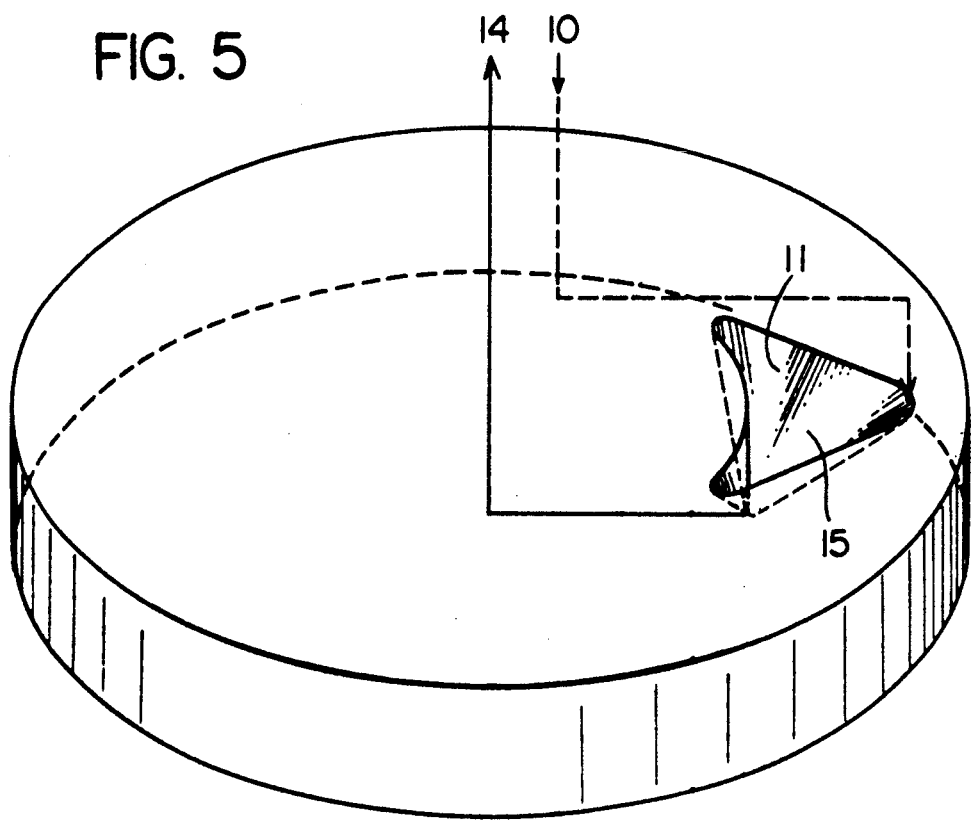

METHOD OF CULTURING ANIMAL CELLS

This application is a continuation in-part-application of Ser. No. 07/463,997, filed on Jan. 12, 1990, now abandoned, which is a continuation-in-part application of Ser. No. 06/939,102 filed on Dec. 8, 1986, now abandoned.

This invention relates to a method of culturing animal cells, and more particularly, to a method of culturing animal cells in suspension.

Cell culture technology is important for the production of antiviral agents such as viral vaccines and interferons or biochemicals such as hormones. The recent production of monoclonal antibodies having the ability to bind to a particular protein as a target relies on the culture of a hybridoma obtained by fusing antibody-producing cells with myeloma cells, and the solution of problems associated with this technique is an industrially important subject.

Heretofore, cell culture has been carried out on a laboratory scale by using a Petri dish, a test tube, a culture bottle, etc.

Some methods and apparatuses for cell culture have recently been suggested. They are roughly classified into anchorage-dependent culture systems and suspension culture systems selected according to the properties of a particular cell to be cultured.

A suspension cell culture method was proposed in which a spinner flask is given an agitating function by a magnetic stirrer or by a vane wheel on a mechanically driven shaft (see U.S. Pat. Nos. 2,958,517 and 3,649,465).

Japanese Laid-Open Patent Publication No. 65180/1982 proposed a suspension culture apparatus in which at least one flexible sheet of a relatively large area supported on a rotatable shaft is used as an agitator and the desired gentle agitation is created for a certain kind of feeble cells such as human diploid cells by rotating the agitator sheet and thus causing it to undulate. In cell culture by this apparatus, the cells are cultured in a fixed amount of nutrients, and the growth of the cells stops while they are at a relatively low cell density.

To prevent the growth of cells from stopping at a relatively low cell density and to culture the cells in large quantities at a high density in suspension, there was proposed a so-called perfusion method comprising culturing cells while supplying a makeup culture medium to a culture tank and in the meantime, discharging the spent medium containing a growth-inhibitory substance out of the tank. In performing culture by this method, it is important to separate the spent medium efficiently from living cells in the suspension and discharge the spent medium out of the tank, and thereby to maintain the growth environment for the cells in the tank under optimum conditions. Various filters or other systems have been proposed for the separation of living cells and the spent medium from the suspension. None of them, however, have proved to be entirely satisfactory for industrial practice because of one or more disadvantages such as the blockage of the filters or the complexity of the structure of the systems.

Japanese Laid-Open Patent Publications Nos. 82083/1984 and 9482/1985 proposed an apparatus for culturing suspended cells at a high density which comprises a culture supernatant discharging tube concurrently functioning as a cell settling tube and a line for addition of a fresh medium so that the cell culture is effected while adding the fresh medium from the line and simultaneously discharging the culture supernatant from the discharge tube.

Generally, suspended animal cells are as small as several microns to several tens of microns in size, and their specific gravity is not much different from that of the culture medium. Hence, in the aforesaid apparatus adapted for separating the suspended cells from the spent medium, the settling area should be increased to settle the cells advantageously. In the apparatuses disclosed in the above two Japanese patent documents, however, the settling area cannot be made so large as is desired.

U.S. Pat. No. 4,814,278, of which inventorship overlaps that of the present application proposes an industrial apparatus and an industrial method which are suitable for the culture of cells in large quantities at a high density by the perfusion technique. This apparatus comprises a cell settling zone, an opening for discharging a spent culture medium from the settling zone and an opening for supplying a fresh culture medium to the suspension culture zone, the suspension culture zone and the settling zone being separated by a partition therebetween in a manner to communicate with each other in the lower portion of the settling zone, and the settling zone being formed between the side wall of the cell culture tank and the partition.

It is an object of this invention to provide a method of culturing animal cells comprising a simple step of separating living animal cells from a suspension culture fluid containing the animal cells.

Another object of this invention is to provide a method of culturing animal cells comprising a step of withdrawing a part of a suspension culture fluid of animal cells from a culture tank and subjecting the withdrawn culture fluid to an operation of separating living animal cells.

Another object of this invention is to provide a method of culturing animal cells, which comprises returning animal cells separated from part of a suspension fluid of animal cells to a culture tank, meanwhile removing the spent culture fluid from which the animal cells have been separated, and introducing fresh supply of culture fluid to the culture tank in an corresponding to the amount of the removed culture fluid.

Another object of this invention is to provide an industrial efficient cultivating method by the perfusion technique in which a large amount of a suspension culture fluid containing animal cells at a high density can be used.

Another object of this invention is to provide a method of culturing animal cells which comprises a step of efficiently separating animal cells which are susceptible to deformation and rupture by an external force unlike microorganisms and yeasts from a culture fluid containing them by using a centrifugal separating device while the animal cells are kept alive.

Another object of this invention is to provide a method of culturing animal cells which comprises a step of performing the aforesaid separation using a centrifugal separating device having a characteristic structure in a sedimentation surface for the animal cells under the action of a centrifugal force.

Another object of this invention is to provide a method of cultivating animal cells which comprises a step of efficiently withdrawing animal cells separated from a centrifugal separating device while they are kept alive.

Another object of this invention is to provide an industrially advantageous method alternately separating animal cells as they are living from the suspension cultivation fluid in a centrifugal separating device and withdrawing the living animal cells separated and accumulated from the centrifugal separating device with a specific liquid medium.

Another object of this invention is to provide a centrifugal separating device suitable for use in the above method.

Further objects and advantages of this invention will become apparent from the following description.

These objects and advantages of this invention are achieved by a method of culturing animal cells, which comprises (A) subjecting living animal cells to suspension culture in a culture tank, (B) withdrawing a portion of a suspension culture fluid containing the living animal cells from the culture tank, (C) supplying the withdrawn suspension culture fluid to a centrifugal separating device and separating the living animal cells from the suspension culture fluid, the centrifugal separating device being operated under the following conditions $$\theta \leq 300, \tag{1}$$

$$\bar{Z} \times \theta \leq 3 \times 10^4, \tag{2}$$

$$Q/S.\bar{Z} \leq 0.3, \text{ and} \tag{3}$$

$$5 \leq \bar{Z} \leq 2,000 \tag{4}$$

wherein
- $\theta$ is the average residence time (minutes) of the animal cells in the centrifugal separating device,
- $\bar{Z}$ is a centrifuging effect,
- Q is the amount (ml/min.) of the suspension culture fluid supplied to the centrifugal separating device per unit time, and
- S is the sedimentation area (cm$^2$) when the centrifugal force is acting, (D) withdrawing the separated living animal cells from the centrifugal separating device, and (E) recycling at least a portion of the withdrawn living animal cells to the culture tank for the step (A).

FIGS. 1A and 1B, 2A and 2B, and 3A and 3B are views showing the concept of a rotor (separating tank) of a centrifugal separating device suitable for use in this invention.

FIG. 4A and 4B show another example of the rotor in the centrifugal separating device used in this invention.

FIG. 5 is a perspective view of the rotor of FIG. 4.

Figure 13:
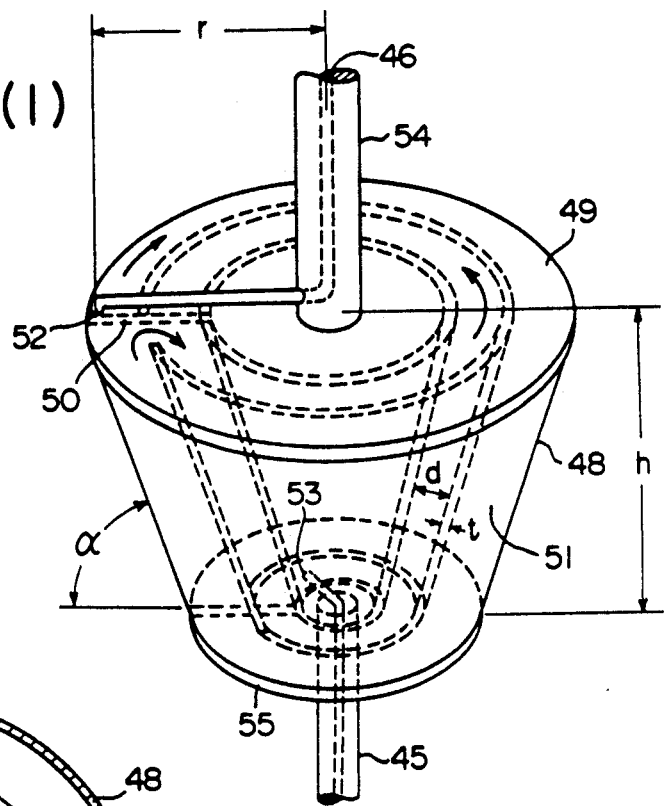
Figure 13:
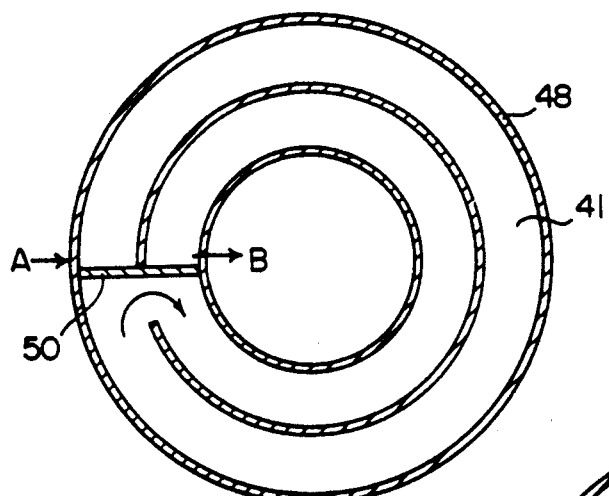
Figure 13:
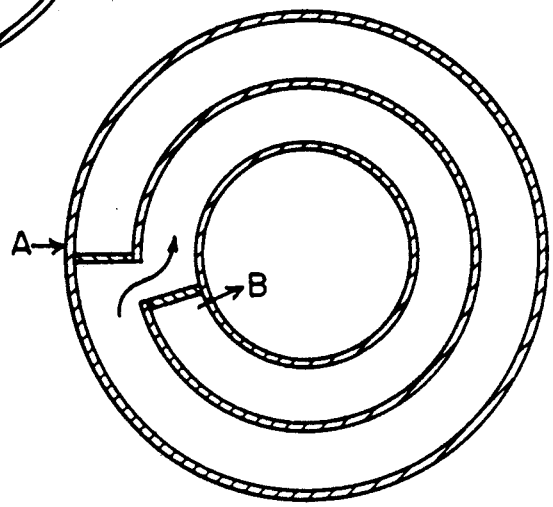

FIGS. 13(1), 13(2) and 13(3) depict perspectives of a culture system having a cell separating unit.

The method of culturing animal cells in accordance with this invention is applicable to the culturing of animal cells in suspension (suspension culture). The suspension culture denotes a method whereby animal cells are cultured while they are floating in an aqueous medium.

The animal cells to which the culturing method of this invention can be applied are those which can grow or proliferate in suspension. They include not only natural animal cells, but also cells modified artificially or by gene manipulation such as hybridoma cells. Or they may be cells derived from lymphatic cells which produce lymphokine, diploid cells producing biologically active substances such as interferon (IFN), or cells producing various monoclonal antibodies.

The present invention is especially suitable for obtaining monoclonal antibodies at high densities by culturing monoclonal antibody-producing cells.

In step (A) of the method of this invention, the animal cells are cultured in suspension in a culture tank. The culture medium used in the suspension culture is an aqueous medium consisting substantially of water. The aqueous medium contains various additives ordinarily used in the culturing of animal cells, for example inorganic salts, vitamins, coenzymes, glucose, amino acids, antibiotics, and growth promoting factors.

Serum may be added to the culture fluid. But a serum-free culture medium may also be used as the culture fluid. The use of the serum-free culture medium is economically advantageous, and therefore desirable.

The culture tank that can be used in this invention at least comprises an opening for feeding animal cells, an opening for introducing a fresh culture medium, a tube for introduction of air, an agitator, and a conduit for withdrawing the suspension culture fluid. Such a culture tank may be an ordinary culture tank.

In step (B), a portion of the suspension culture fluid containing animal cells is withdrawn from the culture tank, for example through a culture fluid withdrawal conduit. The withdrawal of the suspension culture fluid can be carried out continuously or intermittently. Desirably, a fresh supply of the makeup culture medium is introduced into the culture tank continuously or intermittently in an amount corresponding to the amount of the withdrawn suspension culture fluid containing animal cells. As a result, the concentration of substances which inhibit (adversely affect) the growth of the animal cells and consist mainly of metabolites of the animal cells in the suspension culture fluid within the culture tank can be always maintained at a considerably low level. Thus, the density of the grown animal cells in the suspension culture fluid be increased.

The amount of useful metabolites produced with the growth of the animal cells can be increased by an amount corresponding to the increased density of the grown animal cells.

By maintaining the concentration of the substances which inhibit the growth of the animal cells at a low level with a sufficient control, the culturing can be continued while maintaining an increased density of the grown animal cells over an extended period of time, and the useful metabolites can be produced in increased amounts.

The suspension culture fluid containing animal cells which has been withdrawn from the culture tank is then fed to a centrifugal separating device in step (C) wherein the animal cells are separated.

The withdrawn suspension culture fluid may be fed into the centrifugal separating device at a time in a treatable amount, or continuously in small portions.

Components containing the separated animal cells and the spent culture medium may be taken out continuously from the centrifugal separating device while the centrifugal separating device is rotating, or after the rotation of the centrifugal separating device is stopped.

Step (C) of the method of this invention can be especially advantageously performed industrially by a method which comprises continuously feeding a fresh suspension culture medium to the centrifugal separating device in small portions and withdrawing the components containing the separated animal cells and the spent culture medium separately but continuously in small portions (to be preferred to as the continuous method); or a method which comprises continuously feeding the fresh suspension culture medium into the centrifugal separating device and continuously withdrawning the separated spent culture medium in small portions, stopping the feeding of the culture fluid after the lapse of a certain period of time, and thereafter withdrawing the components containing the separated animal cells (to be referred to as the intermittent method).

The centrifugal separating device used in practicing step (C) may be a commercially available device. For example, there can be used a two-component simultaneous recovering type continuous centrifuging system of Hitachi (a large-capacity cooling centrifuge 6PR-52 having an SRR5CT rotor or an SRR3CA rotor built therein). In these commercial centrifuges, the space which will be charged with a fluid to be centrifugally separated is disposed cylindrically around the axis of rotation. According to these centrifugal separators, the animal cells centrifugally separated are sedimented substantially uniformly on a cylindrical sedimenting surface.

Investigations of the present inventors have shown that another suitable example of the centrifugal separating device used in step (C) of the method of this invention is a centrifugal separating device comprising (a) an opening for feeding a suspension culture fluid, (b) a sedimentation surface having such a structure that the sedimented animal cells can move along the sedimentation surface, (c) an animal cell gathering portion where the animal cells moved along the sedimentation surface gather, (d) an opening for withdrawing the animal cells from the animal cell gathering portion and (e) a mother liquor discharge opening for discharging the mother liquor of culturing from which the animal cells have been separated.

The above centrifugal separating device is characterized by having the sedimentation surface (b) and the animal cell gathering portion (c). The structure of the sedimentation surface defined in (b) means such a structure that the animal cells which have sedimented on the sedimentation surface do not stay there but can move from the sedimented site to another site along the sedimentation surface by a centrifugal force. Such a structure is typified by a sedimentation surface whose distance to the axis of rotation of a rotating rotor having the sedimentation surface is not equal, but gently varies so that it becomes gradually larger from a site at the shortest distance to a site at the longest distance. The highest centrifugal force acts on the site having the largest distance, and the lowest centrifugal surface, on the site having the shortest distance. A centrifugal force of varying intensities between these two extremities acts on sites between them. Hence, even the animal cells which have sedimented at the site having the shortest distance gradually moves toward sites having a larger distance along the sedimentation surface under the action of a centrifugal force, and soon gather at the site having the largest distance. The animal cell gathering portion (c) is provided at a place where the sedimented animal cells no longer move by the centrifugal force.

The sedimentation surface (b) has such a structure that in one section containing the axis of rotation of a rotor, the distance from the sedimentation surface to the axis of rotation gradually changes. Hence, the animal cells gather very efficiently by the centrifugal force in a very small spot where in a section perpendicular to the axis of rotation, the above site having the shortest distance and the above site having the largest distance from the axis of rotation in one section containing the axis of rotation. If the opening for withdrawing the animal cells is provided at this spot, the animal cells can be withdrawn advantageously.

The centrifugal separating device of course further includes an opening for feeding the culture fluid as described in (a) above, the opening for withdrawing the animal cells and (e) the opening for discharging the culture mother liquor.

The above centrifugal separating device will be described in detail below with reference to the accompanying drawings.

FIGS. 1, 2 and 3 are views showing the concept of a rotor (separating tank) of a centrifugal separating device suitable for use in this invention. In any of these drawings, A is a sectional view taken in a direction at right angles to the axis of rotation, and B is a sectional view taken in a direction parallel to the axis of rotation and including the axis of rotation.

With reference to FIG. 1, the reference numeral 10 represent an opening for feeding the suspension culture fluid to be subjected to separation, and 11 and 11I represent a sedimentation surface for animal cells. The reference numeral 12 represents an animal cell gathering portion; 13, an opening for withdrawing the animal cells which gather in the gathering portion 12; and 14, a mother liquor discharging opening. The opening 10 for feeding the suspension culture fluid is located at a position apart from the axis of rotation of the rotor by a distance r, and the mother liquor discharge opening 14 is provided at a position corresponding nearly to the axis of rotation of the rotor. In FIG. 1, the distance from the axis of rotation of the sedimentation surface of the rotor gradually becomes larger gently from the portion 11' toward the portion 11. Cells which sediment the portion 11' gradually move toward the sedimentation surface by the action of the centrifugal force. As can be well understood from the sedimentation surface is opened from the bottom to the top of the rotor, and the opening at the portion 11 is larger than the opening 11'. By providing such openings, animal cells which sedimented at a site near the top portion of the rotor and animal cells which sedimented at a site near the bottom of the rotor at the portion 11' soon gather at the gathering portion 12. The opening 13 for withdrawal of the animal cells is provided at a site farther from the axis of rotation than the feed opening 10 for the culture fluid by distance R.

The rotor shown in FIG. 2 is basically the same as the rotor shown in FIG. 1 but differs in the following respects. As can be well seen from FIG. 2, A, the rotor has an animal cell sedimentation surface composed of a combination of two sedimentation surfaces 11a and 11b. The two sedimentation surfaces are in such a relation that animal cells sedimented on the sedimentation surface 11a do not substantially move onto the sedimentation surface 11b, and animal cells sedimented on the sedimentation surface 11b do not substantially move on to the sedimentation surface 11a. Hence, the animal cells sedimented onto the sedimentation surface 11a move along the sedimentation surface 11a and arrive at a gathering portion 12a. On the other hand, the animal cells sedimented on the sedimentation surface 11b move along the sedimentation surface 11b and arrive at a gathering portion 12b. There are two openings 13a and 13b for withdrawing the animal cells separated from the gathering portions 12 and 12b. The mother liquor withdrawing opening 14 in the rotor shown in FIG. 2 is located at a position apart from the axis of rotation by distance $r_o$. The distance $r_o$ is smaller than the distance r from the axis of rotation to the opening for feeding the suspension culture fluid.

The rotor shown in FIG. 3 is basically the same as the rotor shown in FIG. 1, but as can be well seen from FIG. 3, A, the sedimentation surface 11 is nearly circular. Since, however, the center of this circle deviates from the center of the axis of rotation of the rotors the animal cells gather at the gathering portion 12 and is withdrawn from the withdrawal opening 13.

The rotors shown in FIGS. 1, 2 and 3 are suitable when they are operated by the continuous method. The rotor of the centrifugal separating device used in this invention may further comprise a separating plate. The separating plate advantageously catches animal cells at a portion relatively near the axis of rotation, for example, at a portion nearer to the axis of rotation than the culture fluid feed opening, and supplies them to the sedimentation surface.

FIG. 4 shows another example of the rotor in the centrifugal separating device used in this invention. This rotor is advantageously used to withdraw the separated animal cells intermittently from the centrifugal separating device.

As can be well seen from FIG. 4, A and FIG. 5, the rotor shown in FIG. 4 has a nearly triangular separating tank 15. While the culture fluid is being fed into the separating tank 15 from the culture fluid feed opening 10 for a predetermined period of time, the mother liquor is withdrawn from the mother liquor withdrawing opening 14, and the centrifugal separating device continues to be operated. It will be well seen from FIG. 4 that the separating tank 15 has such a sedimentation surface structure that animal cells sedimented gather at the gathering portion 12. The feed opening 10 is provided in the vicinity of the gathering portion 12, and the withdrawing opening 14 is connected to the bottom portion of the separating tank 15. After the centrifugal separating device continues to be operated for a certain period of time as above, the feeding of the culture fluid and the withdrawing of the mother liquor are stopped. The mother liquor is introduced into the separating tank 15 from the withdrawing opening 14, and living cells accumulated in the separating tank are withdrawn together with the mother liquor. During the withdrawal of the animal cells, the rotation of the centrifugal separating device may be stopped if desired.

It will be apparent to those skilled in the art that the aforesaid intermittent operation can also be carried out by the centrifugal separating device having the rotor shown in FIG. 1. In this case, the operation of discharging the mother liquor from the mother liquor discharging opening 14 while feeding the culture fluid from the animal cell withdrawing opening is carried out for a certain period of time. Thereafter, the mother liquor is fed to the rotor from the mother liquor discharge opening, and the animal cells accumulated in the rotor are taken out together with the mother liquor from the withdrawal opening 13.

According to the present invention, the centrifugal separating device should be operated under the following operating conditions in order to separate the animal cells efficiently from the culture fluid in which they are suspended while being kept alive. Generally, the animal cells are susceptible to deformation and rupture by an external force. Hence, it is difficult to separate the animal cells efficiently from the culture fluid while they are kept alive. Investigations of the present inventors have shown it is critical that the following operating conditions (1) to (4) should be simultaneously satisfied.

$$\theta \leq 300, \quad (1)$$

$$\bar{Z} \times \theta \leq 3 \times 10^4, \quad (2)$$

$$Q/S.\bar{Z} \leq 0.3, \text{ and} \quad (3)$$

$$5 \leq \bar{Z} \leq 2,000 \quad (4)$$

wherein
 $\theta$ is the average residence time (minutes) of the animal cells in the centrifugal separating device,
 $\bar{Z}$ is a centrifuging effect,
 Q is the amount (ml/min.) of the suspension culture fluid supplied to the centrifugal separating device per unit time, and
 S is the sedimentation area (cm$^2$) when the centrifugal force is acting.

The average residence time ($\theta$, minutes) of the animal cells in the centrifugal separating device should be limited to not more than 300 minutes. If the residence time exceeds 300 minutes, the survival rate of the animal cells becomes markedly low owing, for example, to the deficiency of oxygen. Preferably, the average residence time ($\theta$) is not more than 150 minutes, especially not more than 60 minutes.

For example, in the continuous method comprising continuously feeding the suspension culture fluid into the centrifugal separating device and continuously withdrawing the separated animal cells, the average residence time ($\theta$) of the animal cells in the centrifugal separating device is obtained as a quotient of the volume ($V_A$, cm$^3$) of the space in which the animal cells in the fed suspension culture fluid can exist under centrifugal conditions, divided by the rate ($Q_C$, cm$^3$/min.) of withdrawing components containing the separated animal cells from the centrifugal separating device.

$\bar{Z}$ is the centrifugal effect in the centrifugal separating operation, and is represented by $r\omega^2/g$ in which r is the distance (cm) from the axis of rotation, $\omega$ is the rotating angular speed (radians/sec.), and g is the acceleration of gravity (cm/sec$^2$). The centrifuging effect, as it were, represents the magnitude of e centrifugal force exerted on the animal cells, and is therefore determined by the position (distance r from the axis of rotation) of the culture fluid feed opening for feeding the suspension culture fluid to be fed to the centrifugal separating device for separation. $\bar{Z}$ is in the range of 5 to 2,000. If it is lower than 5, the separating operation is difficult to perform. If it exceeds 2,000, the centrifugal force on the animal cells is too high and the cells are undesirably ruptured markedly. Advantageously, the centrifuging effect ($\bar{Z}$) should be maintained in the range of 10 to 1,000, especially preferably 20 to 300.

The $\bar{Z} \times \theta$ should be maintained at not more than $3 \times 10^4$. If the centrifuging operation is carried out while the $\bar{Z} \times \theta$ value is above the above-specified range, the survival rate of the animal cells decreases gradually by the compaction of the cells themselves. Especially preferably, the $\bar{Z} \times \theta$ value is not more than $2 \times 10^4$.

S (cm$^2$) is the sedimentation area (cm$^2$) under the action of a centrifugal force. S (cm$^2$) is defined as an effective area involved in separation at the site (r cm from the axis of rotation) of the opening for feeding the suspension culture fluid into the centrifugal separating device for separation. When a phantom circle at the site of the feed opening at a distance of r from the axis of rotation does not cross the sedimentation surface, it is obtained as a value of $2\pi rh$ by the site (r) of the feed opening and the height (h) of the liquid surface of the suspension culture fluid at the position of the feed opening. When the phantom circle crosses the sedimentation surface, the effective area decreases to the area of that portion which ranges to the site where the phantom circle crosses the sedimentation surface, and is obtained by multiplying 2 rh by the ratio of the angle to the point of crossing. It should be understood that the height (h) of the liquid surface mentioned above is a vertical distance from the deepest position of the separating tank of the centrifugal separating device.

The value $S.\bar{Z}$ obtained by multiplying the effective area S and the centrifuging effect $\bar{Z}$ is a parameter that shows the separating ability of the centrifugal separating device. In the method of this invention, a value obtained by dividing the amount Q (ml/min.) of the suspension culture fluid supplied to the centrifugal separating device per unit time by this parameter, i.e. $Q/S.\bar{Z}$, should be limited to not more than 0.3, preferably not more than 0.2, especially preferably not more than 0.1.

By ensuring the operating conditions (1) to (4), step (C) of the method of this invention makes it possible to separate living animal cells efficiently at a very high survival rate from the suspension culture fluid.

According to this invention, the separated animal cells are taken out from the centrifugal separating device in step (D). Step (D) can be carried out by continuously withdrawing the separated animal cells in small portions from the centrifugal separating device by the continuous method during operation. Alternatively, it may be carried out by stopping the supplying of the culture fluid in the intermittent method and then withdrawing the separated animal cells.

The animal cells withdrawn while they are alive are partly or wholly returned to the culture tank for suspension culture in step (A). Returning of the animal cells can be conveniently carried out through an animal cell feed opening of the culture tank either continuously or intermittently.

One embodiment of the present invention will be specifically described with reference to FIG. 6.

Figure 6:
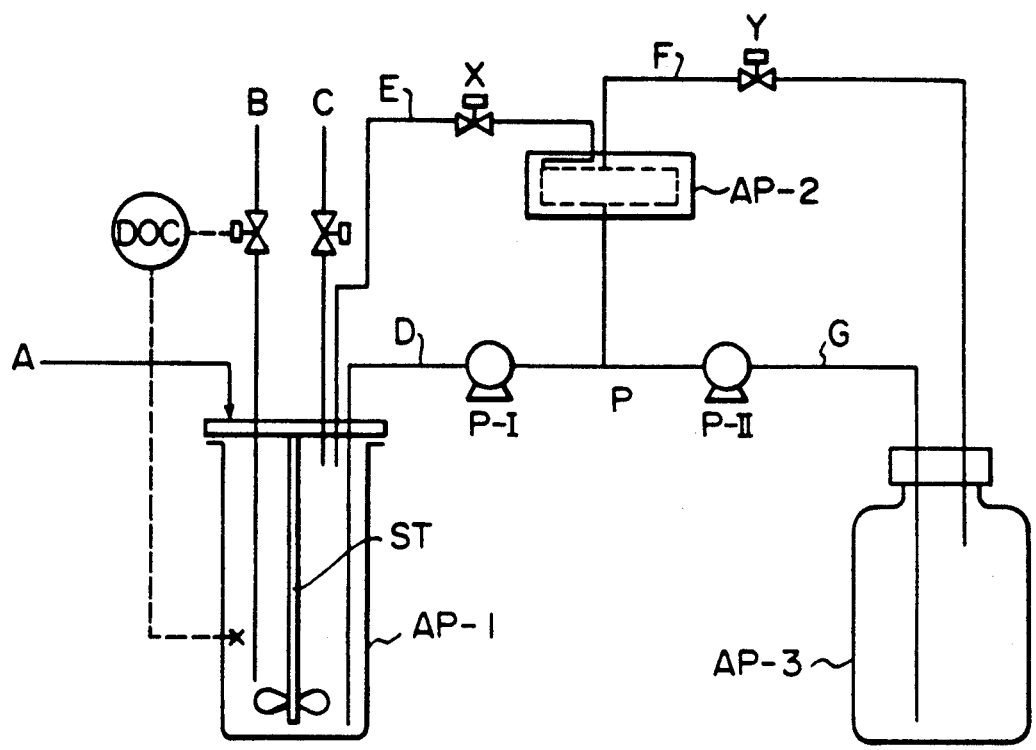
FIGS. 6, 7, 8 and 9 are rough views of a series of devices suitable for carrying out the culture method of this invention.

In the apparatus shown in FIG. 6, a culture tank AP-1 is provided with a feed opening A for feeding a fresh supply of the culture medium, an air (O$_2$) introducing tube B, a dissolved oxygen controller DOC for measuring the oxygen concentration of the culture fluid in the culture tank and adjusting the oxygen concentration of air to be introduced, a stirrer ST, an air exhaust tube C and a withdrawal conduit D for withdrawing the suspension culture fluid. The withdrawal conduit D extends via a pump P-I and bifurcates into two passages. One passage extends to a spent medium vessel AP-3 via a pump P-II and a conduit G. The other is connected to a centrifugal separator AP-2 from which it further extends to the spent medium vessel AP-3 via a conduit F and a valve Y. A conduit E extends from the centrifugal separator AP-2 via a valve X and is connected to the culture tank AP-1.

A fresh supply of the culture medium is fed into the culture tank AP-1 and air is introduced from the air introducing tube B. The stirrer is rotated, and animal cells are seeded in the culture medium to start culturing. When after culturing for a predetermined period of time, the number of cells in the culture tank reached a saturation rotation of the pump P-I is started. The culture fluid in the culture tank is sent to the centrifugal separator AP-2 via the conduit D, and the mother liquor is separated from the animal cells by the centrifugal separator. The separated mother liquor is continuously sent to the spent medium vessel AP-3 via the conduit F. During this time, a fresh supply of the culture medium is introduced from the feed opening A into the culture tank continuously or intermittently so that the liquid surface of the culture tank AP-1 does not much vary. After the centrifugal separator AP-2 is operated for a certain period of time as above, the operation of the pump P-I is stopped. The valve Y is closed and the valve X is opened. The operation of the pump P-II is then started. Consequently, the mother liquor in the spent medium vessel AP-3 is conducted to the centrifugal separator AP-2 via the conduit G, and while carrying the living animal cells accumulated in AP-2, returned to the culture tank AP-1 via the conduit E. By continuously operating the apparatus in this manner, the concentration of substances which inhibit the growth of the animal cells and are accumulated gradually in the culture tank as the animal cells are cultured can be maintained at a low level. Thus, the method of this invention can be practiced advantageously.

Investigations of the present inventors have shown that animal cells separated from the centrifugal separating device can be withdrawn very smoothly and any possibility of causing damage to the animal cells during withdrawal can be reduced greatly by carrying out the separation of the animal cells from the suspension culture fluid in the centrifugal separating device in the presence of a liquid carrier having the following properties:

(a) it is substantially immisicible with water, (b) it has a higher density than water, and (c) it does not substantially inhibit the growth of the animal cells, while the aforesaid operating conditions are ensured.

Since the liquid carrier is substantially immiscible with water (a) and has a higher density than water (b), a liquid phase of the liquid carrier is formed between the culture fluid and the sedimentation surface in the animal cell gathering portion during the operation of the centrifugal separating device. As a result, the animal cells are prevented from being compacted onto the sedimentation surface, and exist on the liquid phase as a cushion. Thus, at the time of withdrawal, the animal cells move separately from or together with, the liquid carrier. Since the liquid carrier does not substantially inhibit the growth of the animal cells, it can exist together with the animal cells without any problem.

Perfluorocarbons, for example, can be suitably used as the liquid carrier. Advantageously, the fluorocarbons are liquid at room temperatures, and commercially available fluorocarbons can be widely utilized. For example, fluorocarbons used as heat media or an electrically insulating material, and various fluorocarbons used as artificial blood may be used. Specific examples include perfluoroalkanes having at least 8 carbon atoms, perfluorocycloalkanes (such as perfluorodecalin, perfluoromethyldecalin, and perfluoroalkylcyclohexane, and perfluoroalkylcyclohexanes having 3 to 5 carbon atoms in the alkyl moiety), perfluoroalkyltetrahydrofurans having 5 to 7 carbon atoms in the alkyl moiety, perfluoroalkyltetrahydropyrans having 4 to 6 carbon atoms in the alkyl moiety, and perfluoroadamantanes (such as perfluoroadamantane, perfluoromethyladamantane, perfluorodimethyladamantane, perfluoromethylethyladamantane and perfluorodiethyladamantane). These perfluorocarbons may contain various groups, for example a tertiary amino group. They may be used either singly or in combination.

Now, with reference to FIG. 7 of the accompanying drawings, the embodiment of this invention using the liquid carrier will be described.

Figure 7:
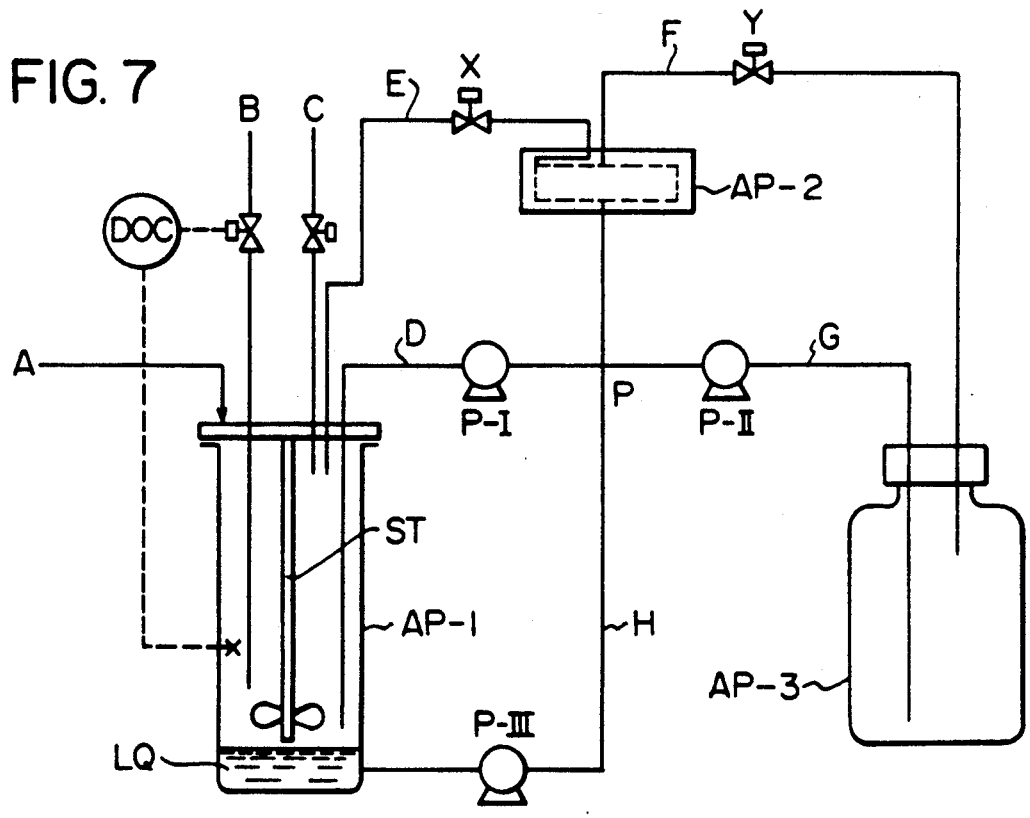

The apparatus of FIG. 7 is basically the same as the apparatus of FIG. 6, and the same reference letters and numerals have the same meanings.

The difference of the apparatus of FIG. 7 from that of FIG. 6 is that a conduit H for withdrawing a liquid carrier phase LQ is disposed at the bottom portion of the culture tank AP-1, and the conduit H extends via the pump P-III and is connected at point P to a conduit extending to the centrifugal separating device AP-2.

In operation, the pump P-III is operated for a short time before the pump P-I is operated to introduce an amount of the liquid carrier LO into the centrifugal separating device AP-2. Then, the pump P-III is stopped, and the same operation as described with reference to the apparatus of FIG. 6 is performed. Since the liquid carrier is partly or wholly introduced into the culture tank AP-1 at the time of withdrawing the separated animal cells from the centrifugal separating device AP-2 through the conduit C, a liquid carrier phase LQ is formed at the bottom of the culture tank. The recyclic use of the liquid carrier phase LQ formed at the bottom of the culture tank is very advantageous to culture on an industrial scale.

According to a preferred embodiment of this invention, the liquid carrier is sent to the centrifugal separating device also at the time of withdrawing the separated animal cells from the centrifugal separating device. In the apparatus shown in FIG. 7, the liquid carrier can be sent to the centrifugal separating device by operating the pump P-III simultaneously with the operation of the pump P-II. This can completely prevent the animal cells from being damaged until the animal cells are withdrawn from the centrifugal separating device.

Investigations of the present inventions have shown that a cultivation method using a liquid carrier, particularly one characterized by the step of separating and withdrawing living animal cells in a centrifugal separating device is industrially advantageous.

Thus, the present invention also provides a method of culturing animal cells, which comprises (A) subjecting living animal cells to suspension culture in a culture tank, (B) withdrawing a portion of the suspension culture fluid containing living animal cells from the culture tank, (C) continuously feeding the withdrawn suspension culture fluid into the centrifuging space of a rotating centrifugal separating device for a certain period of time from a feed opening, and continuously withdrawing the mother liquor separated from the living animal cells for a certain period of time from a discharge opening, the centrifugal force acting on the feed opening being higher than that on the discharge openings and accumulating the living cells in the centrifuging space, (D) feeding a liquid medium which is immiscible with water, has a density higher than the animal cells and the cultivation fluid and does not inhibit the growth of the animal cells into the feed opening while the centrifugal separating device is kept rotating, and withdrawing the living animal cells accumulated in the centrifuging space together with the mother liquor from the discharge opening by pushing them with the liquid medium, and (E) returning at least a portion of the withdrawn animal cells to the culture tank for step (A)

The cultivation method given above comprises steps (A) to (E). Steps (A), (B) and (E) are basically the same as the culture method described earlier in the specification. The characteristic feature of this culture method is that by step (C), living animal cells are accumulated in the centrifuging space of the centrifugal separating device and in the next step (D), the accumulated living animal cells are pushed together with the mother liquor by liquid medium which is immiscible with water, has a higher density than the animal cells and the culture fluid and does not inhibit the growth of the animal cells, and thus withdrawn from the centrifugal separating device.

In step (C), to accumulate the living animal cells, it-is necessary to continuously feed the suspension culture fluid withdrawn in step (B) into the centrifuging space of the centrifugal separating device for a certain period of time and to continuously withdraw the mother liquor separated from the living animal cells for a certain period of time. Specifically, since the suspension culture fluid withdrawn in step (B) has a low concentration of the animal cells, it is fed into the centrifuging space until the animal cells are accumulated in a desired amount. Desirably, the operating conditions for the centrifugal separating device are the same as those described above with regard to the first culture method described hereinabove.

The centrifugal separating device used in this invention has a feed opening and a discharge opening in the centrifuging space. In order that the suspension culture fluid may be conveniently fed and the mother liquor withdrawn continuously for certain periods of time, the centrifugal force acting on the feed opening is higher than that acting on the discharge opening.

As a preferred centrifugal separating device, the present invention provides a centrifugal separator comprising a rotor and a centrifuging space therein, said centrifuging space comprising a peripheral slit having an outside peripheral wall inclining toward the central axis of the rotor at an inclination angle of 50° to 90° in a direction at right angles to the central axis of the rotor, the outside peripheral wall of the peripheral slit drawing a helix with respect to the central axis of the rotor in a phantom plane crossing the central axis of the rotor, and the peripheral slit having a feed opening at, or near, the farthest position from the central axis of the rotor and a discharge opening at, or near the nearest position from the central axis of the rotor.

In the centrifugal separator, the centrifuging space for receiving the suspension culture fluid comprises the peripheral slit provided in the rotor. The peripheral slit has an outside peripheral wall which inclines toward the central axis of the rotor at an inclination angle of 50° to 90°, preferably 60° to 85° in a direction at right angles to the central axis of the rotor. The provision of the outside peripheral wall inclining toward the central axis of the rotor enables the living animal cells separated from the mother liquor to move smoothly over the outside peripheral wall away from the central axis of the rotor. The outside peripheral wall may occupy part or the whole of the outside peripheral wall of the peripheral slit. When it occupies the entire outside peripheral wall of the peripheral slit, the inclination angle of the outside peripheral wall may be the same throughout, or a combination of two or more angles within the above range. In the case of the partial occupation, the outside peripheral wall is preferably comprised of a wall having an inclination angle within the above range and another wall having an inclination angle of less than 50° to a direction at right angles to the central axis of the rotor.

On the other hand, the inside peripheral wall of the peripheral slit does not necessarily have to incline toward the central axis of the rotor. For example, the inside peripheral wall may be parallel, or incline, to the central axis of the rotor. Preferably, the inside peripheral wall, as does the outside peripheral wall, inclines toward the central axis of the rotor at an inclination angle of 50° to 90°, preferably 60° to 85° in a direction at right angles to the central axis of the rotor. Furthermore, the inside peripheral wall may be arcuate or helical, preferably helical, with respect to the central axis of the rotor in a phantom plane crossing the central axis of the rotor.

The peripheral slit can exist within an angular range of not more than 360° or more than 360°, around the central axis of the rotor. When it exists within an angular range of more than 360°, it can exist in the form of a convolution around the central axis of the rotor within the same phantom plane, namely without varying its angle toward the central axis of the rotor. The length of the peripheral slit may be increased by providing the peripheral slit in an angular range of more than 360° around the central axis of the rotor as stated above, and as a result, the animal cells can be separated slowly and smoothly while they are alive. A separating plate for aiding in easy and accurate separation of the animal cells by shortening the sedimentation distance may be provided in the peripheral slit. Such a separating plate is known per se in the art.

The centrifugal separator is provided with a feed opening for feeding the suspension culture fluid and a discharge opening for withdrawing the mother liquor separated from the animal cells during the operation of the centrifugal separator, namely during the rotation of the rotor. The feed opening is formed at, or near, the farthest position from the central axis of the rotor, and the discharge opening at, or near, the nearest position from the central axis of the rotor.

According to the method of this invention, the living animal cells separated by the centrifugal separator and accumulated within the centrifuging space are then pushed out with a liquid medium from the discharge opening together with the mother liquor by supplying the liquid medium from the feed opening in place of the suspension culture fluid into the centrifugal separator in operation [step (D)].

The liquid medium used for this purpose is a liquid medium which is immiscible with water, has a higher density than either the animal cells or the culture fluid, and does not inhibit the growth of the animal cells. For example, perfluorocarbons described hereinbelow can be preferably used as the liquid medium.

The combination of steps (C) and (D) enables the animal cells to be separated while they are alive. Moreover, since the centrifuging space incessantly undergoes washing with the liquid medium, the centrifuging space can be always maintained in an environment which is suitable for the growth of the living animal cells and for an industrially advantageous continuous operation.

At least some of the living animal cells having the ability to proliferate which have been withdrawn in step (D) are returned in step (E) to the culture tank for step (A) by the method of this invention.

By repeating steps (B) to (E), the culture method of this invention produces the above industrial advantages.

The culture method of this invention and the centrifugal separator provided by this invention will now be more specifically described with reference to their preferred embodiments.

Figure 8:
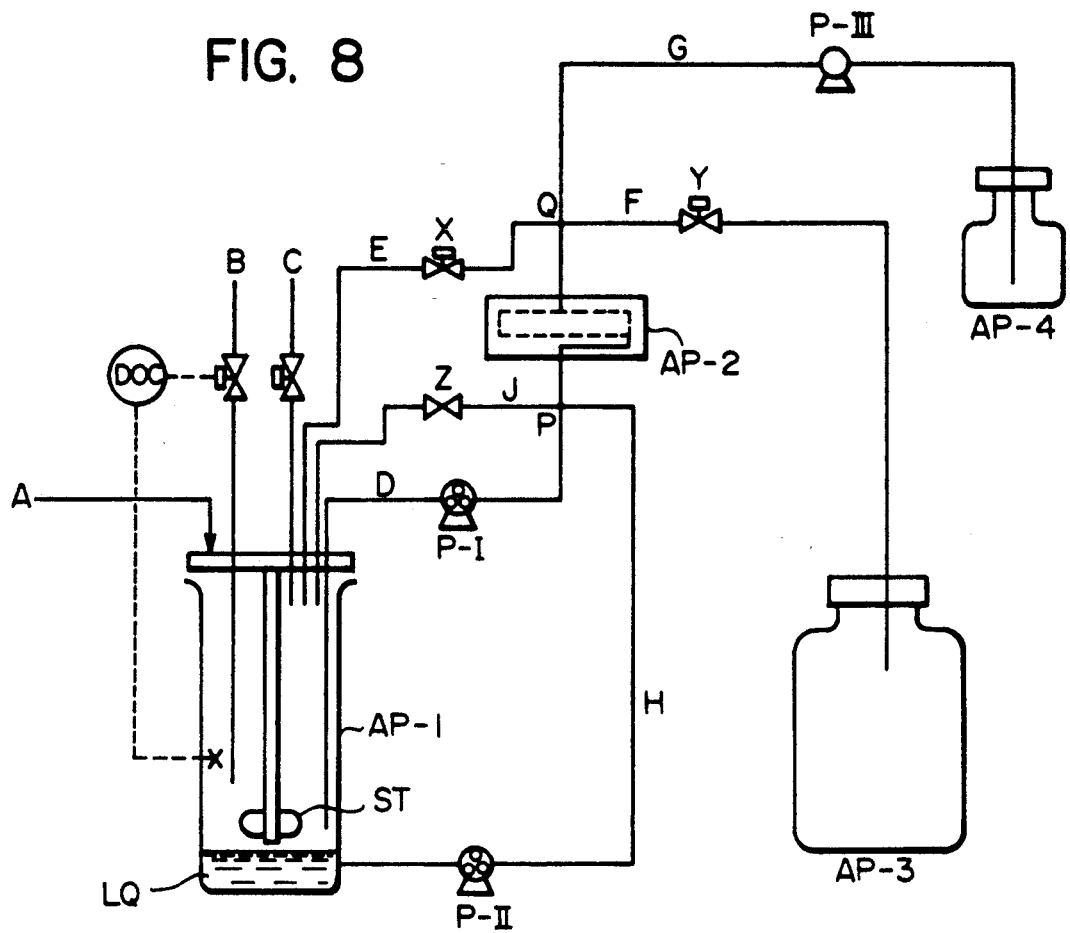

FIG. 8 shows an apparatus suitable for practicing the culture method of this invention.

The apparatus shown in FIG. 8 has a culture tank AP-1 provided with a feed opening A for supplying a fresh culture medium, an air ($O_2$) introduction tube B, a device DOC for measuring the oxygen concentration of the culture fluid in the culture tank and adjusting the oxygen concentration of air to be introduced, a stirrer ST, an exhaust tube C, and a line D for withdrawing the suspension culture fluid. The withdrawing line D is connected to a centrifugal separator AP-2 via a pump P-I.

A line H for withdrawing a liquid substance phase LQ is provided at the bottom portion of the culture tank AP-1. The line H is connected to a line leading to the centrifugal separator QP-2 at point P via a pump P-II.

A line J leading to the culture tank AP-1 through a valve Z is connected at point P. Lines E, F and G are connected at point Q to a conduit extending from the centrifugal separator AP-2.

The line E is connected to the culture tank AP-1 through a valve X; the line F, to a reservoir AP-3 through a valve Y; and the line G, to a fresh medium tank AP-4 through a pump P-III.

A fresh culture medium is charged into the culture tank AP-1, and air is introduced into it through the air introducing tube B. The stirrer is rotated, and by seeding animal cells, the culturing is started. Thereafter, when the number of the animal cells increases to a saturation, the rotation of the pump P-1 is started. The culture fluid within the culture tank is sent to the centrifugal separator AP-2 through the line D. The mother liquor is separated from the animal cells by the centrifugal separator. The separated mother liquor is continuously sent to the reservoir AP-3 through the line F with the valve Y being opened.

During this time, a fresh culture medium is introduced into the culture tank continuously or intermittently from the feed opening A so that the liquid level of the culture tank AP-1 may not greatly vary. After the centrifugal separator AP-2 is operated as above for a certain period of time, the operation of the pump P-I is stopped. The valve Y is closed and the valve X is opened. Then, the operation of the pump P-II is started. As a result, the liquid substance at the bottom portion of the culture tank is conducted to the centrifugal separator AP-2 through the line H, and the living animal cells accumulated in the centrifugal separator AP-2 are pushed out. The liquid substance is returned to the culture tank together with the animal cells. By performing this operation while operating the centrifugal separator, the liquid substance stays in the centrifugal separator, and the cells which have so far resided therein are spontaneously discharged by the difference in gravity. At this time, part or the whole of the liquid substance is sometimes introduced into the culture tank AP-1, and therefore, the liquid substance phase LQ is formed at the bottom portion of the culture tank. It will be seen that the above recycling use of the liquid carrier phase LQ formed in the bottom portion of the culture tank will be very advantageous to industrial-scale culturing.

After the above operation for a certain period of time, the operation of the pump P-II is stopped, the valve X is closed and the valve Z is opened. Then, the operation of the pump P-III is started. As a result, the liquid substance in the centrifugal separator returns to the culture tank. Since the cells does not pass through the liquid substance having a high specific gravity by this operation, the exertion of the unwanted pressure on the cells can be avoided, and damage to the cells can be prevented.

According to this invention, the time during which the animal cells pass through the liquid substance can be reduced to zero or to a very short one. The damage to the animal cells is little if the pressure substantially exerted on the animal cells is 0.2 kgf/cm$^2$ or less. Accordingly, the animal cells are allowed to pass through a liquid substance having a pressure within this pressure range.

By operating this apparatus as described above, the concentration of substances which inhibit the growth of the animal cells accumulated successively within the culture tank as the culturing proceeds can be maintained at low levels.

Figure 9:
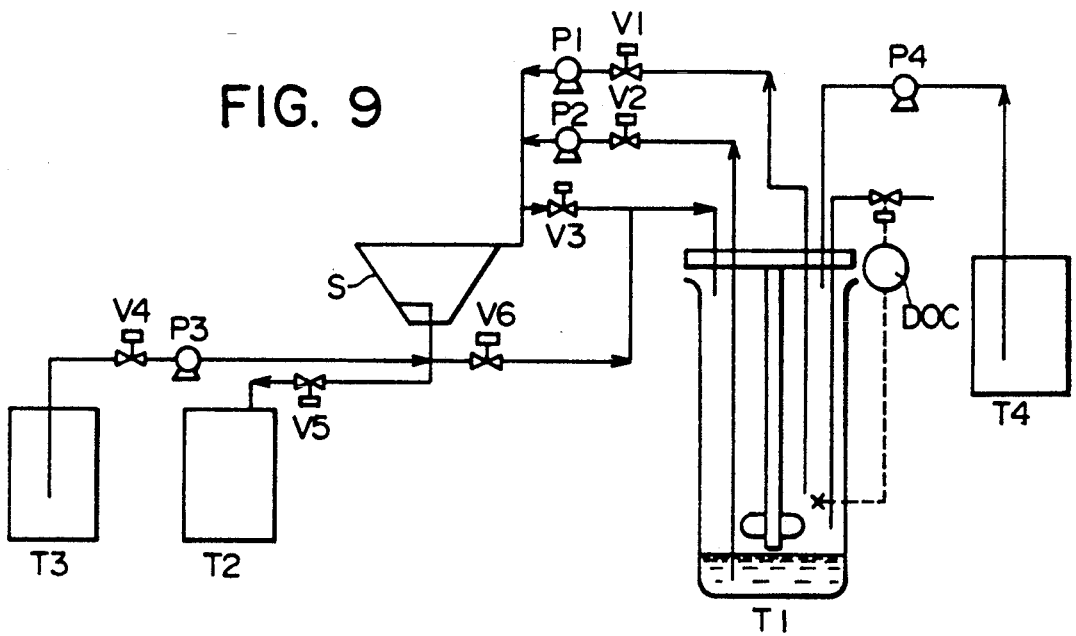

FIG. 9 is an outline view of another apparatus suitable for the practice of the culturing method of this invention.

In FIG. 9, a suspension culture fluid containing animal cells withdrawn from a culture tank T1 by means of a pump P1 is continuously fed into a centrifugal separator S from a feed opening provided at a site under a higher centrifugal force. By the centrifugal force, the animal cells are separated from the suspension culture fluid, and the separated mother liquor is withdrawn continuously and aseptically from a discharge opening provided at a site under a lower centrifugal force, and taken into a tank T2. On that occasion, it is advisable that the suspension fluid flows in laminar form through the peripheral slit. Thereafter, from the bottom portion of the culture tank T1, a liquid which has no affinity for either the cells or the culture fluid and has a higher density than these is withdrawn by a pump P2, and fed in a fixed amount from the feed opening provided at that site of the centrifugal separator S which is under a higher centrifugal force. As a result, the culture fluid containing the separated animal cells in the peripheral slit is aseptically withdrawn from the discharge opening in the centrifugal separator which is at a site under a lower centrifugal force, and returned to the culture tank T1. Thereafter, a cell free medium is withdrawn from the tank T3 by means of the pump P3, and fed from the discharge opening of the centrifugal separator S, whereby the liquid having a higher density in the centrifugal separator is again returned to the culture tank and the inside of the peripheral slit is replaced by the culture medium. A tank T4 contains a fresh cell-free culture medium which is continuously or intermittently fed into the tank T1 by means of a pump P4 so that the liquid level in the culture tank T1 becomes constant.

By performing the above operation continuously or intermittently without stopping the centrifugal separator, the animal cells can be efficiently separated at a very high survival rate. Needless to say, valves V1 to V6 require an opening-closing operation suitable for the above operation.

Figure 10:
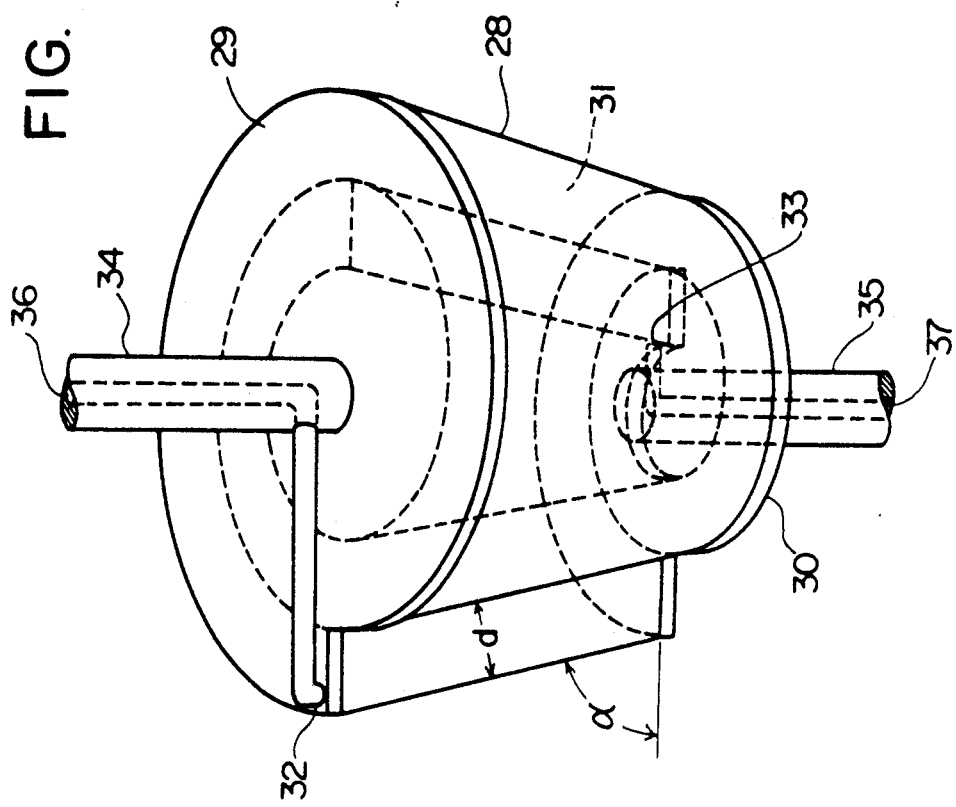
FIG. 10 is a perspective view of an embodiment of the centrifugal separating device of the invention.

FIG. 10 shows a partially perspective view of a centrifugal separator suitable for use in the above culture method.

In FIG. 10, an inside peripheral wall 21 and an outside peripheral wall 22 form a peripheral slit 23. Shown at 24 is an opening for feeding the suspension culture fluid and also for withdrawing the liquid having a higher density. Shown at 25 is an opening for withdrawing the cell-free mother liquor and the culture fluid containing the separated cells. Nozzles 26 and 27 are also provided for feeding into the rotor and/or withdrawal from the rotor.

The angle α between the slit surface and the centrifugal direction in FIG. 10 is preferably 50° to 90°, and the depth d of the peripheral slit is preferably 3 to 5 mm. The surface of the inside surface of the peripheral slit is desirably treated so as to render it hydrophobic. This treatment may be suitably carried out by coating it with a fluorine-containing resin such as polytetrafluoroethylene.

The angle α' between the upper side of the peripheral slit 23 and the centrifugal direction in FIG. 10 is preferably 5° to 10°, and the angle α" between the lower side of the slit and the centrifugal direction is preferably 0° to 5°.

Figure 11:
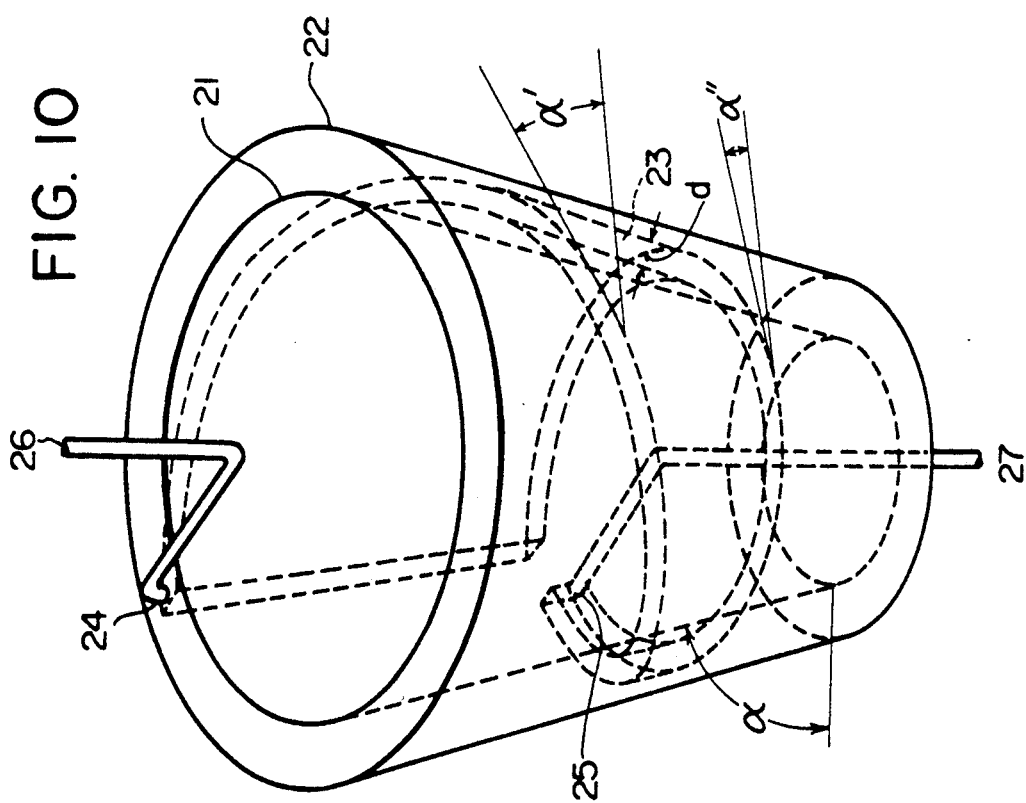
FIGS. 11 and 12 are partially perspective views of other examples of the centrifugal separating devices of the invention.

FIG. 11 shows a partial perspective view of another embodiment of the centrifugal separator of the invention.

In FIG. 11, a peripheral slit 31 is defined by a plate 28 having inclined equidistantly spaced convolutions and flat plates 29 and 30. Shown at 32 is an opening for feeding the suspension culture fluid and also for withdrawing the liquid having a higher density, and the opening 32 is connected to a rotating shaft 34. An opening 33 is for withdrawing the cell-free mother liquor and the culture fluid containing the separated cells, and is also connected to a rotating shaft 35. Nozzles 36 and 37 are provided for feeding into the rotor and/or withdrawal from the rotor. The angle between the surface of the slit and the centrifugal direction in FIG. 11 is preferably 50° to 900°, and the width d of the helical peripheral slit is preferably 3 to 5 mm.

As in the embodiment shown in FIG. 10, the inside wall surface of the slit is preferably treated to render it hydrophobic and thus to avoid adhesion of the cells. Furthermore, to increase the efficiency of separation, a separating plate may be provided in the peripheral slit.

Figure 12:
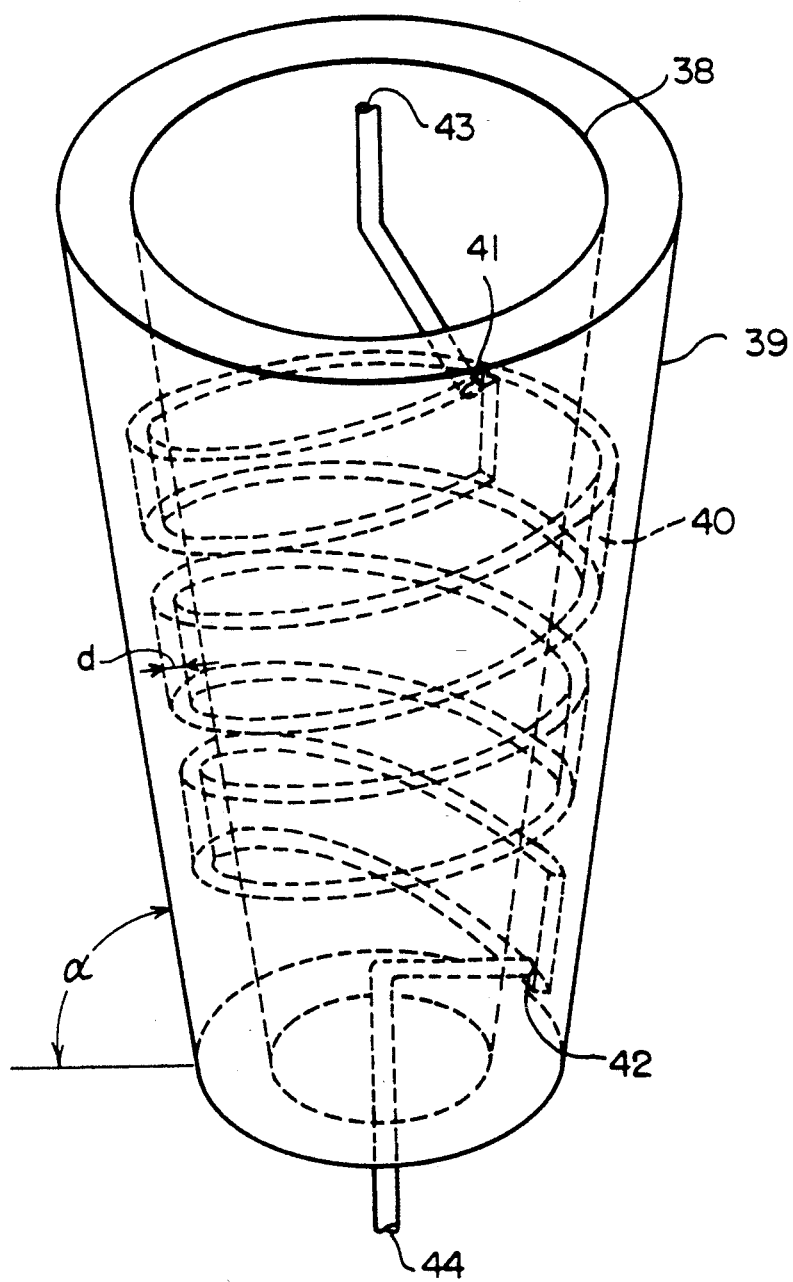

FIG. 12 is a partial perspective view showing still another embodiment of the centrifugal separator of the invention.

In FIG. 12, a peripheral slit 40 is formed of an inside peripheral wall 38 and an outside peripheral wall 39. Shown at 41 is an opening for feeding the suspension culture fluid and also for withdrawing the liquid having a high density. An opening 42 is for withdrawing the cell-free mother liquor and the culture fluid containing the separated animal cells. Nozzles 43 and 44 are provided for feeding into the rotor and/or withdrawal from the rotor.

The angle α between the sat surface and the centrifugal direction in FIG. 12 is preferably 50° to 90°, and the depth d of the peripheral slit is preferably 3 to 5 mm. Likewise, it is effective to render the inside wall surface of the peripheral slit hydrophobic and thus to avoid adhesion of the animal cells.

CONSTRUCTION OF THE INVENTION

According to further study of the present inventors, this invention also provides a centrifugal separator characterized in that (i) a centrifugal space consists of a peripheral slot having an outside peripheral wall inclining toward a central axis of a rotor at an inclination angle of 30° to 80° in a direction perpendicular to the central axis of the rotor, (ii) the peripheral slot exists within an angular range of not less than 360° around the central axis of the rotor, (iii) the peripheral slot has such a space that the liquid fluid forms a continuous flow, (iv) the peripheral slot has a feed opening or a discharge opening of the liquid fluid at, or near, the farthest position from the central axis of the rotor, and (v) the peripheral slot has a feed opening or a discharge opening of the liquid fluid at, or near, the nearest position from the central axis of the rotor.

FIG. 13(1) shows a partially perspective rough view of another centrifugal separator in this invention. In said FIG. 13(1), a peripheral slot is characterized in that it exists to form an inversely helical continuous flow toward the central axis of the rotor substantially without changing the angle. Namely, a centrifugal (direction perpendicular to the central axis) sectional plan view is shown in FIG. 13(2). In said FIG. 13(1), the peripheral slot consists of an equidistantly convoluted plate 48 having an inclination angle (α), a partition plate 50 and flat plates 55, 49 for closing. Reference numeral 52 is a feed opening of a liquid fluid such as a suspension culture fluid, which opening is connected with a rotary shaft 54. The feed opening 52 is indicated at A in FIG. 13(2). Reference numeral 53 is a discharge opening of the separated liquid fluid, which opening is connected with a rotary shaft 45. The discharge opening 53 is indicated at B in FIG. 13(2). From FIGS. 13(1) and 13(2), it follows that in this centrifugal separator, the peripheral slot is formed such that the liquid fluid fed from the feed opening 52 (or B) forms a 360° (nearly one round) continuous flow toward the central axis of the rotor along the rotating direction without changing the angle, the flow is inverted toward the inside from the partition plate located near the feed opening to form again a 360° (nearly one round) continuous flow in the opposite direction to the rotating direction, and the liquid fluid is thereby discharged from the discharge opening 53 (or B). For simplicity of explanation, a structure of a double peripheral slot which means one inversion of a liquid fluid flow is shown in FIGS. 13(1) and 13(2). This invention is however not limited thereto, and a structure with two to five inversions of the liquid fluid flow is also available. Reference numerals 46 and 47 are nozzles for feeding into, and discharging from, the rotor body. In FIG. 13(1), the angle (a) between the slot surface and the centrifuging direction is 30° to 80°, and the depth (d) of the peripheral slot is 2 to 10 mm.

As explained in FIGS. 12, 11, 13(1), 13(2) and 13(3), the centrifugal separator of this invention is characterized in that a centrifuging space consists of a peripheral slot having an outside peripheral wall inclining toward a central axis of a rotor at an inclination angle of 30° to 80° in a direction perpendicular to the central axis of the rotor, the outside peripheral wall of the peripheral slot exists within an angular range of not less than 360° around the central axis of the rotor, the peripheral slot has such a space that the liquid fluid forms a continuous flow, and said peripheral slot has a feed opening or a discharge opening of the liquid fluid at, or near, the farthest position from the central axis of the rotor, and a feed opening or a discharge opening of the liquid flow at, or near, the nearest position from the central axis of the rotor.

It will be explained hereinafter that animal cells are separated from an animal cell-containing suspension culture fluid by the aforesaid centrifugal separator.

A centrifuging space for receiving the suspension culture fluid consists of a peripheral slot provided in a rotor. The peripheral slot has an outside peripheral wall inclining toward the central axis of the rotor at an inclination angle of 30° to 80°, preferably 35° to 75° in a direction perpendicular to the central axis of the rotor, whereby the separated living animal cells can smoothly be moved on the outside peripheral wall in a direction away from the central axis of the rotor, making it possible to prevent them from being diffused again by the liquid flow.

Moreover, even in separating the accumulated animal cells by pushing them out with a liquid carrier to be described later, the animal cells liable to remain in the peripheral slot, especially, on its inside peripheral wall can completely be withdrawn from inside the peripheral slot because of the inclining outside peripheral wall.

The angle of the outside peripheral wall may be the same throughout, or a combination of two or more angles within the above angular range.

Meanwhile, the inside peripheral wall of the peripheral slot, unlike the outside peripheral wall, does not necessarily have to incline toward the central axis of the rotor. For example, the inside peripheral wall may be parallel, or incline, to the central axis of the rotor. The inside peripheral wall, preferably inclines toward the central axis of the rotor, like the outside peripheral wall, at an inclination angle of 30° to 80°, preferably 35° to 75° in a direction perpendicular to the central axis of the rotor. The inside peripheral wall can be helical to the central axis of the rotor in a phantom plane across the central axis of the rotor.

The peripheral slot exists within a length of the outside wall corresponding to an angular range of not less than 360° around the central axis of the rotor. The desirous length of the outside wall varies with the diameter of the rotor. It is usually at least 720° but at most 3600°, most preferably at least 1080° but at most 2520° around the central axis of the rotor. That is, the peripheral slot can be helical around the central axis of the rotor within the same phantom plane, i.e. without changing the angle toward the central axis of the rotor (e.g. FIG. 11). Alternatively, it can be helical, inclining around the central axis of the rotor at a certain inclination angle toward the central axis of the rotor (e.g. FIG. 12). The length of the peripheral slot can be increased, as stated above, by providing the peripheral slot having a length corresponding to an angular range of not less than 360° around the central axis of the rotor. Consequently, the separation of the living animal cells can be carried out slowly, smoothly and efficiently. The peripheral slot may be provided therein with a separation plate for aiding in easy and accurate separation of the animal cells by shortening the sedimentation distance. Such separating plate is known per se in the art.

The centrifugal separator is provided in the centrifuging space, i.e. the peripheral slot with a feed opening for feeding the suspension culture fluid and a discharge opening for withdrawing the mother liquor separated from the animal cells during operation of the centrifugal separator, i.e. during rotation of the rotor. The feed opening is formed at, or near, the farthest position from the central axis of the rotor of the peripheral slot; the discharge opening is formed at, or near, the nearest position from the central axis of the rotor of the peripheral slot.

The feed or discharge opening of the liquid fluid formed at, or near, the nearest position from the central axis of the rotor is desirably situated in at least ⅓ of the radius of the rotor from the central axis of the rotor.

The centrifugal separator of this invention is thus provided in the space with the peripheral slot, and said peripheral slot has the outside peripheral wall inclining at the inclination angle toward the central axis of the rotor and is of a structure to form a long continuous flow. The centrifugal separator is therefore quite suited to treat an animal cell-containing suspension and separate the animal cell therefrom. That is, because the substantial area of the peripheral slot can be taken in a quite wide range with respect the centrifugal separator of the same scale and the laminar flow be formed in the peripheral slot for smooth flow of the suspension, the damage of the animal cells can be extremely minimized.

The centrifugal separator of this invention can thus be said to have such a structure that the substantial area of the peripheral slot for separation is wide and the smooth flow is formed. In other words, the centrifugal separator of this invention has the quite excellent structure to treat the suspension containing animal cells susceptible to damage by exertion of a pressure or physical operation in large quantities per unit time and unit volume (substantial volume of the centrifugal separator) and to separate the living animal cells.

Moreover, according to the study of the present inventors, there are provided [I] a method of separating animal cells and an aqueous solution from a living animal cell-containing suspension using the centrifugal separator of this invention, and [III] a method of culturing animal cells in suspension.

[I] Method of Separating Animal Cells and an Aqueous Solution from a Living Animal Cell-Containing Suspension A method of separating animal cells and an aqueous solution from a living animal cell-containing aqueous suspension, which comprises (A) feeding a living animal cell-containing aqueous suspension from a feed opening of a liquid fluid in (iv) in the rotating centrifugal separator of this invention for a certain period of time, meanwhile withdrawing the aqueous solution separated from the living animal cells from a discharge opening of the liquid fluid in (v), and accumulating the animal cells in the space of the centrifugal separator, (B) then feeding a liquid carrier immiscible with water, having a higher density than the animal cells and the aqueous solution and not inhibiting the growth of the animal cells from the feed opening of the liquid fluid in (iv) in the rotating centrifugal separator, withdrawing the living animal cells together with the remaining aqueous solution by pushing them out with the liquid carrier from the discharge opening of the liquid fluid in (v) to thereby obtain the living animal cells, and (C) further feeding a fresh aqueous solution from the feed opening of the liquid fluid in (v) in the rotating centrifugal separator, and withdrawing the liquid carrier from the discharge opening of the liquid fluid in (iv) to separate the liquid carrier.

[III] Method of Culturing Animal Cells in Suspension

A method of culturing animals in suspension, which comprises, (a) culturing living animal cells in suspension in a culture tank, (b) withdrawing a portion of the living animal cell-containing suspension culture fluid from the culture tank, (c) feeding the withdrawn suspension culture fluid from the feed opening of the liquid fluid in (iv) in the rotating centrifugal separator of this invention for a certain period of time, meanwhile withdrawing the culture fluid separated from the living cells via the discharge opening of the liquid fluid in (v), and accumulating the animal cells in the space of the centrifugal separator, (d) then feeding a liquid carrier immiscible with water, having a higher density than the animal cells and the culture fluid and not inhibiting the growth of the animal cells from the feed opening of the liquid fluid in (iv) in the centrifugal separator, and withdrawing the living animal cells by pushing them out together with the culture fluid from the discharge opening of the liquid fluid in (v), (e) returning at least a portion of the withdrawn animal cells to the culture tank for step (a), and (f) further feeding a fresh culture fluid or the culture fluid withdrawn in step (c) from the feed opening of the liquid fluid in (v) in the centrifugal separator, and withdrawing the liquid carrier from the discharge opening of the liquid fluid in (iv) to recover the liquid carrier from the centrifugal separator by separation.

In the separating method [II], the "living animal cell-containing aqueous suspension" being separated can be any solution containing the animal cells in suspension, and its origin is not limited in particular. It may be a suspension withdrawn from a culture tank in suspension culture of animal cells, or body fluids of mammals, especially blood.

The operation of the culturing method [III] in this invention will be explained hereinafter. Said method is not substantially different from the separating method [I]. That is, steps (c), (d) and (f) in the method [III] correspond to steps (A), (B) and (C) in the method [I].

The above culturing method is characterized by accumulating the living animal cells in the centrifuging space of the centrifugal separator in step (c), and then pushing and withdrawing the accumulated living animal cells together with the mother liquor by the liquid medium immiscible with water, having a higher density than the animal cells and the culture fluid and not hindering the growth of the animal cells in step (d).

In step (c), to accumulate the living animal cells, it is necessary to continuously feed the suspension culture fluid withdrawn in step (b) into the centrifuging space of the centrifugal separator for a certain period of time and to continuously withdraw the mother liquor separated from the living animal cells for a certain period of time. Specifically, since the suspension culture fluid withdrawn in step (b) has a low concentration of the animal cells, it is fed into the centrifuging space until the animal cells are accumulated for the centrifugal separator are desirable.

$$\theta \leq 300, \tag{1}$$

$$\bar{Z} \times \theta \leq 3 \times 10^4 \tag{2}$$

$$Q/S.\bar{Z} \leq 0.3, \text{ and} \tag{3}$$

$$5 \leq \bar{Z} \leq 2,000 \tag{4}$$

wherein $\theta$ is the average residence time (minutes) of the animal cells in the centrifugal separator, $\bar{Z}$ is a centrifuging effect, Q is the amount (ml/min.) of the suspension culture fluid supplied to the centrifugal separator per unit time, and S is the sedimentation area (cm$^2$) when the centrifugal force is acting.

The average residence time ($\theta$, minutes) of the animal cells in the centrifugal separator should be limited to not more than 300 minutes. If the residence time exceeds 300 minutes, the survival rate of the animal cells becomes markedly low owing, for example, to the deficiency of oxygen. Preferably, the average residence time ($\theta$) is not more than 150 minutes, especially not more than 60 minutes. Most preferable is not more than 30 minutes but not less than 5 minutes.

For example, in the continuous method comprising continuously feeding the suspension culture fluid into the centrifugal separator and continuously withdrawing the separated animal cells, the average residence time ($\theta$) of the animal cells in the centrifugal separator is obtained as a quotient of the volume (V, cm$^3$) of the space in which the animal cells in the fed suspension culture fluid can exist under centrifugal conditions, divided by the rate ($Q_C$, cm$^3$/min.) of withdrawing components containing the separated animal cells from the centrifugal separator.

$\bar{Z}$ is the centrifugal effect in the centrifugal separator, and is represented by r $^2$/g in which r is the distance (cm) from the axis of rotation, is the rotating angular speed (radians/sec$^2$), and g is the acceleration of gravity (cm/sec$^2$). The centrifuging effect, as it were, represents the magnitude of e centrifugal force exerted on the animal cells, and is therefore determined by the position (distance r from the axis of rotation) of the culture fluid feed opening for feeding the suspension culture fluid to be fed to the centrifugal separator for separation. $\bar{Z}$ is in the range of 5 to 2,000. If it is lower than 5, the separating operation is difficult to perform. If it exceeds 2,000, the centrifugal force on the animal cells is too high and the cells are undesirably ruptured markedly. Advantageously, the centrifuging effect ($\bar{Z}$) should be maintained in the range of 10 to 1,000, especially preferably 20 to 300.

The $\bar{Z} \times \theta$ should be maintained at not more than $3 \times 10^4$. If the centrifuging operation is carried out while the $\bar{Z} \times \theta$ value is above the above-specified range, the survival rate of the animal cells decreases gradually by the compaction of the cells themselves. Especially preferably, the $\bar{Z} \times \theta$ value is not more than $2 \times 10^4$.

S (cm$^2$) is the sedimentation area (cm$^2$) under the action of a centrifugal force. S (cm$^2$) is defined as an effective area involved in separation at the site (r cm from the axis of rotation) of the opening for feeding the suspension culture fluid into the centrifugal separator for separation. When a phantom circle at the site of the feed opening at a distance of r from the axis of rotation does not cross the sedimentation surface, it is obtained as a value of 2 rh by the site (r) of the feed opening and the height (h) of the liquid surface of the suspension culture fluid at the position of the feed opening. When the phantom circle crosses the sedimentation surface, the effective area decreases to the area of that portion which ranges to the site where the phantom circle crosses the sedimentation surface, and is obtained by multiplying $2\pi rh$ by the ratio of the angle to the point of crossing. It should be understood that the height (h) of the liquid surface mentioned above is a vertical distance from the deepest position of the separating tank of the centrifugal separator.

The value $S.\bar{Z}$ obtained by multiplying the effective area S and the centrifuging effect $\bar{Z}$ is a parameter that shows the separating ability of the centrifugal separator. In the method of this invention, a value obtained by dividing the amount Q (ml/min.) of the suspension culture fluid supplied to the centrifugal separator per unit time by this parameter, i.e. $Q/S.\bar{Z}$, should be limited to not more than 0.3, preferably not more than 0.2, especially preferably not more than 0.1.

By ensuring the operating conditions (1) to (4), step (C) of the method of this invention makes it possible to separate living animal cells efficiently at a very high survival rate from the suspension culture fluid.

The living animal cells separated by the centrifugal separator and accumulated in the centrifuging space is then, in step (d) according to the above method of this invention, pushed out from the discharge opening together with the mother liquor by feeding a liquid carrier immiscible with water, having a higher density than the animal cells and the culture fluid and not inhibiting the growth of the animal cells to the centrifugal separator in operation from the feed opening instead of the suspension culture fluid.

Perfluorocarbons, described in above, can be suitably used as the liquid carrier.

The combination of steps (c) and (d) enables the animal cells to be separated while they are alive. Moreover, since the centrifuging space incessantly undergoes washing with the liquid carrier, the centrifuging space can always be maintained in an environment suited for the growth of the living animal cells and for an industrially advantageous continuous operation.

At least a portion of the living animal cells having the ability to proliferate which have been withdrawn in step (d) are then, in step (e) according to the culturing method of this invention, returned to the culture tank for step (a).

Moreover, in this invention, in step (f), the fresh culture fluid or the culture fluid withdrawn in step (c) is fed from the feed opening of the liquid fluid in (v) of the rotating centrifugal separator, and the liquid carrier is withdrawn from the discharge opening of the liquid fluid in (iv) to recover it from the centrifugal separator by separation.

The culturing method of this invention is an industrially profitable method that exhibits the aforesaid advantages by repeating steps (b) to (f).

As is apparent from the foregoing explanation, the culturing method of this invention is said to be a method which employs the centrifugal separator of the aforesaid structure and uses the liquid carrier immiscible with water, having a higher density than the animal cells and the aqueous solution and not inhibiting the growth of the animal cells, to thereby exhibit the functions thereof most effectively.

That is, in the culturing method of this invention shown in FIG. 9, the liquid carrier in the bottom portion of the culture tank is introduced into the centrifugal separator S via the pump P2, the living animal cells accumulated in the centrifugal separator S are thereby pushed out and returned to the culture tank together with the cells. By performing the operation while driving the centrifugal separator, the liquid carrier stays in the centrifugal separator, and the cells which have so far resided therein are spontaneously discharged owing to difference in specific gravity. on this occasion, part or the whole of the liquid carrier is sometimes introduced into the culture tank T1, and therefore the liquid carrier phase is formed at the bottom portion of the culture tank. It will be seen that the above recycling use of the liquid carrier phase formed in the bottom portion of the culture tank is quite advantageous to industrial-scale culturing.

Since the cells do not pass through the liquid carrier having a higher specific gravity by this operation, the exertion of the unnecessary pressure on the cells is avoidable, and damage to the cells is preventable.

According to this invention, the time during which the animal cells pass through the liquid carrier can be reduced to zero or to a very short one. The damage to the animal cells is little if the pressure substantially exerted on the animal cells is 0.2 kgf/cm² or less. The animal cells are therefore allowed to pass through a liquid carrier having a pressure within this pressure range.

Moreover, by operating this apparatus as described above, the concentration of substances which inhibit the growth of the animal cells accumulated successively within the culture tank as the culturing proceeds can be maintained at low levels.

The following examples illustrate the method of this invention in greater detail.

EXAMPLE 1

(1) Culture Device

A culture system of the type shown in FIG. 6 was used. The culture tank (AP-1) was a glass stirred culture tank having a total capacity of 2 liters and adapted to receive 1.2 liters as a net volume of the culture fluid. AP-2 in FIG. 6 is a centrifugal separator with a rotor having an effective volume of 11 ml and a sedimentation area S of 31.4 cm². Pumps P-I and P-III are peristaltic pumps.

(2) Culture Medium

A 2:1:1 mixture of RPMI, 1640 medium, Ham-12 medium and Dulbeccos' modified Eagle medium (to be referred to as RDF) was used as a base medium.

A culture medium was prepared by adding 2 micrograms/ml of insulin, 10 micrograms/ml of transferrin, 10 micrograms/ml of ethanolamine and $2 \times 10^{-8}$ mole/-liter of selenous acid to the base medium.

(3) Method and Result of Culture

The culture system was sterilized in advance by autoclaving. 1.2 liters of the medium sterilized by filtration was fed into the culture tank, and mouse-mouse hybridoma 4C10B6 cells derived from mouse myeloma P3UI were seeded at a density of $2 \times 10^5$ cells/ml. These hybridoma cells produce IgG. Oxygen gas containing 5% of carbon dioxide gas was introduced into the culture tank through a blow nozzle B while the concentration of dissolved oxygen in the culture fluid was automatically controlled to 3 ppm. The culture fluid in the culture tank was maintained at 37° C. A marine-type stirring vane was attached to the cultivation tank, and operated at a stirring speed of 60 rpm.

For four days after seeding, the culturing was carried out batchwise. As shown in Table 1, the cell density reached $1.0 \times 10^6$ cells/ml on the fourth day after starting the culturing. This density was determined to be the maximum density in batch culture, and perfusion culture using a centrifugal separator was then started. The centrifugal separator charged with the filtrationsterilized culture fluid was driven, and the rotation speed of the centrifugal separator was adjusted so that the centrifuging effect became 10 G. Then, valve X was closed, pump P-II was stopped, and valve Y was opened. In this state, pump P-I was operated to send 200 ml of the culture fluid to the centrifugal separator for 10 minutes at a rate of 20 ml/min. The mother liquor separated from the cells in the centrifugal separator was sent to the spent medium vessel AP-3 through line F and stored. In the spent medium vessel AP-3, the cell density was $2.4 \times 10^5$ cells/ml. After the lapse of 5 minutes from the termination of the foregoing operation, valve X was opened, valve Y was closed and pump P-I was stopped. In this stage, pump P-II was operated to send 50 ml of the spent medium to the centrifugal separator from vessel AP-3 at a rate of 10 ml/min. By this operation, all cells residing in the centrifugal rotor were discharged from the centrifugal separator, and returned to the culture tank AP-1 via the line E. Mter 50 ml of the spent medium was sent, the pump P-II was stopped. The culturing was continued by performing this operation automatically once every period of time indicated in Table 1. A fresh supply of the culture medium was continuously fed into the culture tank from line A so that the liquid level of the culture tank was constant. On the fifth day after the starting of the culturing and thereafter, the culture fluid containing cells was withdrawn from the culture tank at a rate of 120 ml per day. In the above experiment, $Q/S.\overline{Z}$ was 0.064 cm/min.; $\theta$ was 12.5 min., and $\overline{Z}.\theta$ was 125.

Some of the experimental conditions and the results of the experiment are shown in Table 1. In the table, the ratio of the make-up medium means the number of feedings of the makeup medium to be fed per day on the basis of the effective culture volume.

TABLE 1

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $2 \times 10^5$ | 0 |
| 1 | — | 0 | $3.1 \times 10^5$ | 4 |
| 2 | — | 0 | $6.1 \times 10^5$ | 11 |
| 3 | — | 0 | $1.0 \times 10^6$ | 28 |
| 4 | 3 | 1.0 | $2.3 \times 10^6$ | 37 |
| 5 | 3 | 1.0 | $3.8 \times 10^6$ | 41 |
| 6 | 2 | 1.5 | $6.4 \times 10^6$ | 53 |
| 7 | 2 | 1.5 | $8.2 \times 10^7$ | 62 |
| 8 | 1.5 | 2.0 | $1.0 \times 10^7$ | 57 |
| 9 | 1.5 | 2.0 | $1.1 \times 10^7$ | 61 |

EXAMPLE 2

(1) Culture Apparatus

The same apparatus as in Example 1 was used.

(2) Culture Medium

There was used a culture medium obtained by adding 9 micrograms/ml of insulin, 10 micrograms/ml of transferrin, 10 micrograms/ml of ethanolamine and $2 \times 10^{-10}$ mole/liter of selenous acid to the same base medium as in Example 1.

(3) Method and Result of Culturing

The culture system was sterilized by autoclaving. Then, 1.2 liters of the culture medium sterilized by filtration was fed into the culture tank. Then, mouse-human hybridoma H-2 cells obtained by fusing mouse myeloma P3U1 cells with human B cells were seeded at a density of $5 \times 10^5$ cells/ml. These hybridoma cells produce IgG. oxygen-gas containing 5% of carbon dioxide gas was introduced by a blow nozzle B into the culture tank so that the concentration of dissolved oxygen in the culture fluid was maintained at 3 ppm by automatic control. The culture fluid-in the culture tank was maintained at 37° C. A marine-type stirring vane was attached to the culture tank, and its stirring speed was 60 rpm.

For 3 days after seeding, batchwise culture was performed. As shown in Table 2, the cell density reached $1.0 \times 10^6$/ml on the third day after starting the culture (after the lapse of 24 hours), the cell density reached $1.0 \times 10^6$ cells/ml. Since this cell density was determined to be the highest density in batchwise culture, and perfusion culture using a centrifugal separator was started. A centrifugal separator charged with the filtration-sterilized culture fluid was driven, and the rotation speed of the centrifugal separator was adjusted so that the centrifuging effect became 20 G. Then, valve X was closed, pump P-II was stopped, and valve Y was opened. In this state, pump P-I was operated to send 200 ml of the culture fluid to the centrifugal separator for 10 minutes at a rate of 20 ml/min. The mother liquor separated from the cells in the centrifugal separator was sent to the spent medium vessel AP-3 through line F and stored. In the spent medium vessel AP-3, the cell density was $1.8 \times 10^5$ cells/ml. After the lapse of 5 minutes from the termination of the foregoing operation, valve X was opened, valve Y was closed and pump P-I was stopped. In this state, pump P-II was driven to send 50 ml of the spent medium to the centrifugal separator from vessel AP-3 at a rate of 10 ml/min. By this operation, the cells residing in the centrifugal rotor were all discharged from the centrifugal separator, and returned to the culture tank AP-1 via the line E. After 50 ml of the spent medium was sent, the pump P-II was stopped. The culturing was continued by performing this operation automatically once every period of time indicated in Table 2. A fresh supply of the culture medium was continuously fed into the culture tank from line A so that the liquid level of the culture tank was constant. On the fourth day after the starting of the culturing and thereafter, the culture fluid containing cells was withdrawn from the culture tank at a rate of 120 ml per day. In the above experiment, $O/S.\bar{Z}$ was 0.032 cm/min.; $\theta$ was 12.5 min., and $\bar{Z}.\theta$ was 250.

Some of the experimental conditions and the results of the experiment are shown in Table 2.

TABLE 2

| Culturing time (days) | Time interval for feeding to the centrifugal separator (minutes) | Number of feedings of the makeup medium per day | Density of living cells (cells/ml) | Concentration of the antibody in the culture fluid (μg/ml) |
| --- | --- | --- | --- | --- |
| 0 | — | 0 | $5 \times 10^5$ | 0 |
| 1 | — | 0 | $7 \times 10^5$ | 4 |
| 2 | — | 0 | $1.0 \times 10^6$ | 15 |
| 3 | 3 | 1.0 | $1.7 \times 10^6$ | 26 |
| 4 | 2 | 1.5 | $3.0 \times 10^6$ | 21 |
| 5 | 1.5 | 2.0 | $4.9 \times 10^6$ | 22 |
| 6 | 1.0 | 3.0 | $7.8 \times 10^6$ | 28 |
| 7 | 0.5 | 6.0 | $1.1 \times 10^7$ | 19 |
| 8 | 0.5 | 6.0 | $1.3 \times 10^7$ | 25 |
| 9 | 0.5 | 6.0 | $1.1 \times 10^7$ | 31 |
| 10 | 0.5 | 6.0 | $1.4 \times 10^7$ | 29 |

EXAMPLE 3

(1) Culture Apparatus

The same apparatus as in Example 1 was used.

(2) Culture Medium

The same culture medium as in Example 2 was used.

(3) Method and Result of Culturing

The culture system was sterilized by autoclaving. Then, 1.2 liters of the culture medium sterilized by filtration was fed into the culture tank. Then, mouse-mouse hybridoma V-6 cells obtained by fusing mouse myeloma P3U1 cells with human B cells were seeded at a density of $5 \times 10^5$ cells/ml. These hybridoma cells produce IgG. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vahe was attached to the culture tank, and its stirring speed was 60 rpm.

For 3 days after seeding, batchwise culture was performed. As shown in Table 3, the cell density reached $1.1 \times 10^6$/ml on the third day after starting the culture. Since this cell density was determined to be the highest density in batchwise culture, and perfusion culture using a centrifugal separator was started. A centrifugal separator charged with the filtration-sterilized culture fluid was driven, and the rotation speed of the centrifugal separator was adjusted so that the centrifuging effect became 50 G. The valve X was closed, pump P-II was stopped, and valve Y was opened. In this state, pump P-I was operated to send 200 ml of the culture fluid to the centrifugal separator for 4 minutes at a rate of 50 ml/min. The mother liquor separated from the cells in the centrifugal separator was sent to the spent medium vessel AP-3 through line F and stored. In the spent medium vessel AP-3, the cell density was $0.7 \times 10^5$ cells/ml. After the lapse of 5 minutes from the termination of the foregoing operation, valve X was opened, valve Y was closed and pump P-I was stopped. In this state, 50 ml of the spent medium was sent to the centrifugal separator at a rate of 10 ml/min. By this operation, the cells residing in the centrifugal rotor were all discharged from the centrifugal separator, and returned to the culture tank AP-1 via the line E. After 50 ml of the spent medium was sent, the pump P-II was stopped. The culturing was continued by performing this operation automatically once every period of time indicated in Table 3. A fresh supply of the culture medium was continuously fed into the culture tank from line A so that the liquid level of the culture tank was constant. On the fourth day after the starting of the culturing and thereafter, the culture fluid containing cells was withdrawn from the culture tank at a rate of 120 ml per day. In the above experiment, $Q/S.\bar{Z}$ was 0.032 cm/min.; $\theta$ was 4.5 min., and $\bar{Z}.\theta$ was 225.

Some of the experimental conditions and the results of the experiment are shown in Table 3.

TABLE 3

| Culturing time (days) | Time interval for feeding to the centrifugal separator (minutes) | Number of feedings of the makeup medium per day | Density of living cells (cells/ml) | Concentration of the antibody in the culture fluid ($\mu$g/ml) |
|---|---|---|---|---|
| 0 | — | 0 | $5 \times 10^5$ | 0 |
| 1 | — | 0 | $7.1 \times 10^5$ | 2 |
| 2 | — | 0 | $1.1 \times 10^6$ | 6 |
| 3 | 90 | 2 | $1.8 \times 10^6$ | 5 |
| 4 | 90 | 2 | $2.9 \times 10^6$ | 7 |
| 5 | 45 | 4 | $3.9 \times 10^6$ | 6 |
| 6 | 45 | 4 | $7.1 \times 10^6$ | 9 |
| 7 | 45 | 4 | $9.2 \times 10^6$ | 10 |
| 8 | 33 | 5.5 | $1.2 \times 10^6$ | 9 |
| 9 | 33 | 5.5 | $1.3 \times 10^6$ | 11 |

EXAMPLE 4

(1) Culture Apparatus

The same apparatus as in Example 1 was used.

(2) Culture Medium

The same culture medium as in Example 2 was used.

(3) Method and Result of Culturing

The culture system was sterilized by autoclaving. Then, 1.2 liters of the culture medium sterilized by filtration was fed into the culture tank. Then, mouse-human hybridoma H-2 cells were seeded at a density of $5 \times 10^5$ cells/ml. These hybridoma cells produce IgG. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vane was attached to the culture tank, and its stirring speed was 60 rpm.

For 3 days after seeding, batchwise culture was performed. As shown in Table 4, the cell density reached $0.9 \times 10^6$/ml on the third day after starting the culture. Since this cell density was determined to be the highest density in batchwise culture, and perfusion culture using a centrifugal separator was started. A centrifugal separator charged with the filtration-sterilized culture fluid was driven, and the rotation speed of the centrifugal separator was adjusted so that the centrifuging effect became 100 G. The valve X was closed, pump P-II was stopped, and valve Y was opened. In this state, pump P-I was operated to send 200 ml of the culture fluid to the centrifugal separator for 2 minutes at a rate of 100 ml/min. The mother liquor separated from the cells in the centrifugal separator was sent to the spent medium vessel AP-3 through line F and stored. In the spent medium vessel AP-3, no cell was seen to exist. After the termination of the foregoing operation, valve X was opened, valve Y was closed and pump P-I was stopped. In this state, pump P-II was driven to send 50 ml of the spent medium to the centrifugal separator at a rate of 25 ml/min. By this operation, the cells residing in the centrifugal rotor were all discharged from the centrifugal separator, and returned to the culture tank AP-1 via the line E. After 50 ml of the spent medium was sent, the pump P-II was stopped. The culturing was continued by performing this operation automatically once every period of time indicated in Table 4. A fresh supply of the culture medium was continuously fed into the culture tank from line A so that the liquid level of the culture tank was constant. On the fourth day after the starting of the culturing and thereafter, the culture fluid containing cells was withdrawn from the culture tank at a rate of 120 ml per day. In the above experiment, $Q/S.\bar{z}$ was 0.032 cm/min.; $\theta$ was 2 min. and $\bar{Z}.\theta$ was 200.

Some of the experimental conditions and the results of the experiment are shown in Table 4.

TABLE 4

| Culturing time (days) | Time interval for feeding to the centrifugal separator (minutes) | Number of feedings of the makeup medium per day | Density of living cells (cells/ml) | Concentration of the antibody in the culture fluid ($\mu$g/ml) |
|---|---|---|---|---|
| 0 | — | 0 | $5 \times 10^5$ | 0 |
| 1 | — | 0 | $7.1 \times 10^5$ | 4 |
| 2 | — | 0 | $9 \times 10^5$ | 14 |
| 3 | 95 | 1.9 | $1.7 \times 10^6$ | 19 |
| 4 | 45 | 4 | $3.1 \times 10^6$ | 14 |
| 5 | 45 | 4 | $6.1 \times 10^6$ | 17 |
| 6 | 32 | 5.6 | $8.3 \times 10^6$ | 21 |
| 7 | 26 | 7 | $9.8 \times 10^6$ | 19 |
| 8 | 26 | 7 | $1.3 \times 10^7$ | 21 |
| 9 | 26 | 7 | $1.4 \times 10^7$ | 24 |
| 10 | 26 | 7 | $1.4 \times 10^7$ | 23 |

EXAMPLE 5

(1) Culture Apparatus

The same apparatus as in Example 1 was used.

(2) Culture Medium

The same culture medium as in Example 2 was used.

(3) Method and Result of Culturing

The culture system was sterilized by autoclaving. Then, 1.2 liters of the culture medium sterilized by filtration was fed into the culture tank. Then, mouse-human hybridoma 4C10B6 cells were seeded at a density of $2 \times 10^5$ cells/ml. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vane was attached to the culture tank, and its stirring speed was 60 rpm.

For 4 days after seeding, batchwise culture was performed. As shown in Table 5, the cell density reached $0.89 \times 10^6$/ml on the third day after starting the culture. Since this cell density was determined to be the highest density in batchwise culture, and perfusion culture using a centrifugal separator was started. A centrifugal separator charged with the filtration-sterilized culture fluid was driven, and the rotation speed of the centrifugal separator was adjusted so that the centrifuging effect became 500 G. The valve X was closed, pump P-II was stopped, and valve Y was opened. In this state, pump P-I was operated to send 200 ml of the culture fluid to the centrifugal separator for 2 minutes at a rate of 100 ml/min. The mother liquor separated from the cells in the centrifugal separator was sent to the spent medium vessel AP-3 through line F and stored. In the spent medium vessel AP-3, no cell was seen to exist. After the termination of the foregoing operation, valve X was opened, valve Y was closed and pump P-I was stopped. In this state, pump P-II was driven to send 50 ml of the spent medium to the centrifugal separator at a rate of 25 ml/min. By this operation, the cells residing in the centrifugal rotor were all discharged from the centrifugal separator, and returned to the culture tank AP-1 via the line E. After 50 ml of the spent medium was sent, the pump P-II was stopped. The culturing was continued by performing this operation automatically once every period of time indicated in Table 5. A fresh supply of the culture medium was continuously fed into the culture tank from line A so that the liquid level of the culture tank was constant. On the fifth day after the starting of the culturing and thereafter, the culture fluid containing cells was withdrawn from the culture tank at a rate of 120 ml per day. In the above experiment, $Q/S.\bar{Z}$ was 0.006 cm/min.; $\theta$ was 2 min., and $\bar{Z}.\theta$ was 1,000.

Some of the experimental conditions and the results of the experiment are shown in Table 5.

TABLE 5

| Culturing time (days) | Time interval for feeding to the centrifugal separator (minutes) | Number of feedings of the makeup medium per day | Density of living cells (cells/ml) | Concentration of the antibody in the culture fluid ($\mu$g/ml) |
|---|---|---|---|---|
| 0 | — | 0 | $5 \times 10^5$ | 0 |
| 1 | — | 0 | $6.8 \times 10^5$ | 5 |
| 2 | — | 0 | $8.9 \times 10^5$ | 13 |
| 3 | 95 | 1.9 | $1.7 \times 10^6$ | 21 |
| 4 | 45 | 4 | $3.0 \times 10^6$ | 15 |
| 5 | 45 | 4 | $5.9 \times 10^6$ | 18 |
| 6 | 32 | 5.6 | $8.4 \times 10^6$ | 24 |
| 7 | 26 | 7 | $9.6 \times 10^6$ | 23 |
| 8 | 26 | 7 | $1.4 \times 10^7$ | 28 |
| 9 | 26 | 7 | $1.3 \times 10^7$ | 21 |
| 10 | 26 | 7 | $1.5 \times 10^7$ | 24 |

COMPARATIVE EXAMPLE 1

Mouse-mouse hybridoma 4C10B6 cells were cultured under the same conditions except as noted below.
Centrifuging effect: 2,500 G
Rate of sending 200 ml of the culture fluid to the centrifugal separator: 100 ml/min. (for 2 minutes)
After sending the culture fluid as above, the operation of withdrawing the cells was immediately started.
Sending of a cell-free culture medium for withdrawing the cells from the centrifugal separator:
Amount of the medium sent: 50 ml
Rate of sending the medium: 25 ml/min.
In the above experiment, $Q/S.\bar{Z}$ was 0.0016 cm/min., $\theta$ was 2 min., and $\bar{Z}.\theta$ was 5,000.
Some of the experimental conditions and the results of the experiment are shown in Table 6.
The cells were greatly damaged as a result of passage through the centrifugal separator, and the density of the living cells decreased with time. Accordingly, after the lapse of 5 days, the culturing was stopped.

TABLE 6

| Culturing time (days) | Time interval for feeding to the centrifugal separator (hours) | Number of feedings of the makeup medium per day | Density of living cells (cells/ml) | Concentration of the antibody in the culture fluid ($\mu$g/ml) |
|---|---|---|---|---|
| 0 | — | 0 | $2 \times 10^5$ | 0 |
| 1 | — | 0 | $2.9 \times 10^5$ | 5 |
| 2 | — | 0 | $5.9 \times 10^5$ | 10 |
| 3 | — | 0 | $9.7 \times 10^5$ | 29 |
| 4 | 3 | 1.0 | $7.9 \times 10^5$ | 21 |
| 5 | 3 | 1.0 | $4.2 \times 10^5$ | 13 |

COMPARATIVE EXAMPLE 2

Mouse-human hybridoma H-2 cells were cultured under the same conditions as in Example 2 except as noted below.
Centrifuging effect: 30 G
Amount of the culture fluid sent to the centrifugal separator per cycle: 350 ml
Rate of sending the culture fluid: 20 ml/min.
Time required to end the culture fluid: 17.5
Time which elapsed until the withdrawal of the cells from the centrifugal separator was started after 350 ml of the culture fluid was sent to the centrifugal separator: 5.5 hours
In the above experiment, $Q/S.\bar{Z}$ was 0.031 cm/min., $\theta$ was 341 min., and $\bar{Z}.\theta$ was 10238.
After sending of the culture fluid to the centrifugal separator was started, no increase in the density of living cells was noted. Therefore, the culturing was stopped after 7 days.
Some of the experimental conditions and the results of the experiment are shown in Table 7.

TABLE 7

| Culturing time (days) | Time interval for feeding to the centrifugal separator (hours) | Number of feedings of the makeup medium per day | Density of living cells (cells/ml) | Concentration of the antibody in the culture fluid ($\mu$g/ml) |
|---|---|---|---|---|
| 0 | — | 0 | $5 \times 10^5$ | 0 |
| 1 | — | 0 | $7 \times 10^5$ | 6 |
| 2 | — | 0 | $1.1 \times 10^6$ | 17 |
| 3 | 6 | 1.0 | $9.3 \times 10^5$ | 19 |
| 4 | 6 | 1.0 | $7.6 \times 10^5$ | 15 |
| 5 | 6 | 1.0 | $7.2 \times 10^5$ | 14 |
| 6 | 6 | 1.0 | $4.4 \times 10^5$ | 18 |
| 7 | 6 | 1.0 | $6.9 \times 10^5$ | 12 |

COMPARATIVE EXAMPLE 3

Mouse-human hybridoma H-2 cells were cultured under the same conditions as in Example 2 except as noted below.
Centrifuging effect: 1700 G
Amount of the culture fluid sent to the centrifugal separator per cycle: 350 ml
Time which elapsed until the withdrawal of the cells from the centrifugal separator was started after 200 ml of the culture fluid was sent to the centrifugal separator: 12.5 minutes
In the above experiment, $Q/S.\bar{Z}$ was 0.00037 cm/min., $\theta$ was 20 min., and $\bar{Z}.\theta$ was $3.4 \times 10^4$.
Some of the experimental conditions and the results of the experiment are shown in Table 8.
After sending of the culture fluid to the centrifugal separator was started, no increase in the density of living cells was noted. Therefore, the culturing was stopped after 7 days.

TABLE 8

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $5 \times 10^5$ | 0 |
| 1 | — | 0 | $8 \times 10^5$ | 5 |
| 2 | — | 0 | $1.1 \times 10^6$ | 16 |
| 3 | 3 | 1.0 | $8.1 \times 10^5$ | 21 |
| 4 | 3 | 1.0 | $7.1 \times 10^5$ | 15 |
| 5 | 3 | 1.0 | $6.2 \times 10^5$ | 13 |
| 6 | 3 | 1.0 | $5.5 \times 10^5$ | 15 |
| 7 | 3 | 1.0 | $4.7 \times 10^5$ | 11 |

EXAMPLE 6

(1) Culture Apparatus

A culture system of the type shown in FIG. 7 was used. The culture tank AP-1 was a glass stirred culture tank having a total volume of 2 liters and adapted to receive 1.2 liters as the net amount of a culture medium to be fed.

In FIG. 7, AP-2 was a centrifugal separator with a rotor which had a sedimentation area S of 31.4 cm$^2$ and an effective capacity of 11 ml, and pumps P-I, P-II and P-III were peristatic pumps.

(2) Culture Medium

The same culture medium as in Example 2 was used.

(3) Method and Result of Culturing

The culture system was sterilized by autoclaving. Then, 1.2 liters of the culture medium sterilized by filtration was fed into the culture tank. Mouse-human hybridoma H-2 cells obtained by fusing mouse myeloma P3U1 cells and human B cells were seeded at a density of $5 \times 10^6$ cells/ml. The hybridoma cells produce IgG. Oxygen gas containing 5% of carbon dioxide gas was introduced into the culture tank by a blow nozzle B so that the concentration of dissolved oxygen in the culture medium was maintained at 3 ppm by automatic control. The culture fluid in the culture tank was maintained at 37° C. A marine-type stirring vane was attached to the culture tank, and the rate of stirring was 60 rpm.

For 3 days after seeding, the culturing was carried out batchwise. As shown in Table 9, the cell density reached $1.0 \times 10^6$ cells/ml on the third day after the start of the culturing (after the lapse of 24 hours). This density was determined to be the highest density attainable in batchwise culture, and perfusion culture was started using a centrifugal separator. The centrifugal separator charged with the culture fluid sterilized by filtration was driven to adjust the rotating speed so as to provide a centrifuging effect of 100 g. Then, valve X was closed, pumps P-II and P-III were stopped, and valve Y was opened. In this state, the pump P-I was driven, and 200 ml of the culture fluid was sent to the centrifugal separator for 10 minutes at a rate of 20 ml/min. The mother liquor separated from the cells by the centrifugal separator was sent to spent medium vessel AP-3 through line F and stored there. After the lapse of 5 minutes from the end of the above operation, valve X was opened, valve Y was closed, and pump P-I was stopped. In this state, pump P-II was driven, and 50 ml of the spent medium was sent to the centrifugal separators (AP-2) from vessel AP-3 at a rate of 10 ml/min. Pump P-III was driven simultaneously with the driving of pump P-II to send 5 ml of a fluorocarbon in the lower portion of the culture and AP-1 was sent at a rate of 1 ml/min. By this operation all the cells residing in the rotor of the centrifugal separator were discharged from the centrifugal separator together with the fluorocarbon, and returned to the culture tank AP-1. After 50 ml of the culture fluid was sent the pump P-II was stopped. Furthermore, after 5 ml of the fluorocarbon was sent, the pump P-III was stopped. This culturing was continued by performing this operation automatically every period of time indicated in Table 9. A fresh supply of the culture medium was continuously fed from line A so that the liquid level of the culture tank became constant. On the fourth day after the starting of the culturing and thereafter, 120 ml of the culture fluid was withdrawn from the culture fluid per day.

In the above experiment. $Q/S.\bar{Z}$ was 0.032/min., $\theta$ was 12.5 min., and $\bar{Z}.\theta$ was 250.

Some of the experimental conditions and the results of the experiment were shown in Table 9.

TABLE 9

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $5 \times 10^5$ | 0 |
| 1 | — | 0 | $7 \times 10^5$ | 4 |
| 2 | — | 0 | $1.0 \times 10^6$ | 15 |
| 3 | 3 | 1.0 | $1.7 \times 10^6$ | 26 |
| 4 | 2 | 1.5 | $3.0 \times 10^6$ | 21 |
| 5 | 1.5 | 2.0 | $4.9 \times 10^6$ | 22 |
| 6 | 1.0 | 3.0 | $7.8 \times 10^6$ | 28 |
| 7 | 0.5 | 6.0 | $1.1 \times 10^7$ | 19 |
| 8 | 0.5 | 6.0 | $1.3 \times 10^7$ | 25 |
| 9 | 0.5 | 6.0 | $1.1 \times 10^7$ | 31 |
| 10 | 0.5 | 6.0 | $1.4 \times 10^7$ | 29 |

COMPARATIVE EXAMPLE 4

Mouse-human hybridoma H-2 cells were cultured under the same conditions as in Example 6 except that no fluorocarbon was sent to the centrifugal separator.

The living cells became pelletized in the centrifugal separator, and did not return completely to the culture tank. Thus, no increase in the density of living cells was noted. Hence, the culturing was stopped after the lapse of 7 days.

Some of the experimental conditions and the results of the experiment are shown in Table 10.

TABLE 10

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $5 \times 10^5$ | 0 |
| 1 | — | 0 | $8 \times 10^5$ | 5 |
| 2 | — | 0 | $1.1 \times 10^6$ | 16 |
| 3 | 3 | 1.0 | $8.1 \times 10^5$ | 21 |
| 4 | 3 | 1.0 | $7.1 \times 10^5$ | 15 |
| 5 | 3 | 1.0 | $6.2 \times 10^5$ | 13 |
| 6 | 3 | 1.0 | $5.5 \times 10^5$ | 15 |
| 7 | 3 | 1.0 | $4.7 \times 10^5$ | 11 |

EXAMPLE 7

(1) Culture Apparatus

The same culture apparatus as in Example 1 was used.

(2) Culture Medium

The same culture medium as in Example 1 was used.

(3) Method and Result of Culturing

The culture system was sterilized by autoclaving. Then, 1.2 liters of the culture medium sterilized by filtration was fed into the culture tank. Mouse-mouse hybridoma JTC-3 cells were then seeded at a density of $2 \times 10^5$ cells/ml. These hybridoma cells produce IgG. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vane was attached to the culture tank, and its stirring speed was 60 rpm.

For 4 days after seeding, batchwise culture was performed. As shown in Table 11, the cell density reached $1.1 \times 10^6$/ml on the third day after starting the culture. Since this cell density was determined to be the highest density in batchwise culture, and perfusion culture using a centrifugal separator was started. A centrifugal separator charged with the filtrationsterilized culture fluid was driven, and the rotation speed of the centrifugal separator was adjusted so that the centrifuging effect became 80 G. The valve X was closed, pump P-II was stopped, and valve Y was opened. In this state, pump P-I was operated to send 200 ml of the culture fluid to the centrifugal separator for 30 minutes at a rate of 16.7 ml/min. The mother liquor separated from the cells in the centrifugal separator was sent to the spent medium vessel AP-3 through line F and stored. In the spent medium vessel AP-3, the cell density was $2.4 \times 10^5$ cells/ml. Immediately after the termination of the foregoing operation, valve X was opened, valve Y was closed and pump P-I was stopped. In this state, pump P-II was driven to send 55 ml of the spent medium to the centrifugal separator at a rate of 11 ml/min. from the vessel AP-3. By this operation, all cells residing in the centrifugal rotor were discharged from the centrifugal separator, and returned to the culture tank AP-1 via the line E. After 55 ml of the spent medium was sent, the pump P-II was stopped. The culturing was continued by performing this operation automatically once every period of time indicated in Table 11. A fresh supply of the culture medium was continuously fed into the culture tank from line A so that the liquid level of the culture tank was constant. on the fourth day after the starting of the culturing and thereafter, the culture fluid containing cells was withdrawn from the culture tank at a rate of 120 ml per day. In the above experiment, $Q/S.\overline{Z}$ was 0.0027 cm/min.; $\theta$ was 30 min., and $\overline{Z}.\theta$ was 2,400.

Some of the experimental conditions and the results of the experiment are shown in Table 11.

TABLE 11

| Culturing time (days) | Time interval for feeding to the centrifugal separator (hours) | Number of feedings of the makeup medium per day | Density of living cells (cells/ml) | Concentration of the antibody in the culture fluid (μg/ml) |
|---|---|---|---|---|
| 0 | — | 0 | $2.0 \times 10^5$ | 0 |
| 1 | — | 0 | $2.5 \times 10^5$ | 5 |
| 2 | — | 0 | $5.2 \times 10^5$ | 11 |
| 3 | — | 0 | $1.1 \times 10^6$ | 29 |
| 4 | 2.9 | 1.0 | $2.3 \times 10^6$ | 25 |
| 5 | 2.9 | 1.0 | $3.9 \times 10^6$ | 35 |
| 6 | 1.7 | 1.7 | $6.8 \times 10^6$ | 34 |
| 7 | 1.7 | 1.7 | $9.4 \times 10^6$ | 47 |
| 8 | 1.4 | 2.0 | $1.1 \times 10^7$ | 49 |
| 9 | 1.4 | 2.0 | $1.2 \times 10^7$ | 51 |

EXAMPLE 8

(1) Culture Apparatus

The same culture apparatus as in Example 1 was used

(2) Culture Medium

The same culture medium as in Example 1 was used.

(3) Method and Result of Culturing

The culture system was sterilized by autoclaving. Then, 1.2 liters of the culture medium sterilized by filtration was fed into the culture tank. Mouse-human hybridoma P3UI cells derived from mouse myeloma P3UI cells were then seeded at a density of $1.1 \times 10^5$ cells/ml. These hybridoma cells produce IgG. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vane was attached to the culture tank, and its stirring speed was 60 rpm.

For 5 days after seeding, batchwise culture was performed. As shown in Table 12, the cell density roached $5.4 \times 10^5$/ml on the fifth day after starting the culture. Since this cell density was determined to be the highest density in batchwise culture, and perfusion culture using a centrifugal separator was started. The centrifugal separator charged with the filtration-sterilized culture fluid was driven, and the rotation speed of the centrifugal separator was adjusted so that the centrifuging effect became 80 G. The valve X was closed, pump P-II was stopped, and valve Y was opened. In this state, pump P-I was operated to send 200 ml of the culture fluid to the centrifugal separator for 30 minutes at a rate of 6.7 ml/min. The mother liquor separated from the cells in the centrifugal separator was sent to the spent medium vessel AP-3 through line F and stored. In the spent medium vessel AP-3, the cell density was $2.4 \times 10$ cells/ml. Immediately after the termination of the foregoing operation, valve X was opened, valve Y was closed and pump P-I was stopped. In this state, pump P-II was driven to send 55 ml of the spent medium to the centrifugal separator at a rate of 11 ml/min. from the vessel AP-3. By this operation, all cells residing in the centrifugal rotor were discharged from the centrifugal separator, and returned to the culture tank AP-1 via the line E. After 55 ml of the spent medium was sent, the pump P-II was stopped. The culturing was continued by performing this operation automatically once every period of time indicated in Table 12. A fresh supply of the culture medium was continuously fed into the culture tank from line A so that the liquid level of the culture tank was constant. On the sixth day after the starting of the culturing and thereafter, the culture fluid containing cells was withdrawn from the culture tank at a rate of 120 ml per day. In the above experiment, $Q/S.\bar{Z}$ was 0.0027 cm/min.; $\theta$ was 30 min., and $\bar{Z}.\theta$ was 2400.

Some of the experimental conditions and the results of the experiment are shown in Table 12.

TABLE 12

| Culturing time (days) | Time interval for feeding to the centrifugal separator (hours) | Number of feedings of the makeup medium per day | Density of living cells (cells/ml) | Concentration of the antibody in the culture fluid (μg/ml) |
|---|---|---|---|---|
| 0 | — | 0 | $1.1 \times 10^5$ | 0 |
| 1 | — | 0 | $1.0 \times 10^5$ | 2 |
| 2 | — | 0 | $1.9 \times 10^5$ | 4 |
| 3 | — | 0 | $3.6 \times 10^5$ | 7 |
| 4 | — | 0 | $5.4 \times 10^5$ | 10 |
| 5 | 2.9 | 1.0 | $9.8 \times 10^5$ | 11 |
| 6 | 2.9 | 1.0 | $1.9 \times 10^6$ | 14 |
| 7 | 2.9 | 1.0 | $3.5 \times 10^6$ | 16 |
| 8 | 1.7 | 1.7 | $6.4 \times 10^6$ | 17 |
| 9 | 1.7 | 1.7 | $9.2 \times 10^6$ | 19 |
| 10 | 1.4 | 2.0 | $1.3 \times 10^7$ | 20 |
| 11 | 1.4 | 2.0 | $1.2 \times 10^7$ | 23 |

EXAMPLE 9

(1) Culture Apparatus

The same culture apparatus as in Example 1 was used.

(2) Culture Medium

The same culture medium as in Example 1 was used.

(3) Method and Result of Culturing

The culture system was sterilized by autoclaving. Then, 1.2 liters of the culture medium sterilized by filtration was fed into the culture tank. J558L chimera cells which are transformants obtained by introducing human and mouse genes into mouse myeloma J558L as a host were seeded at a density of $1.2 \times 10^5$ cells/ml. These hybridoma cells produce a chimera antibody having a mouse antibody in the V region and a human antibody in the C region. Oxygen gas containing 5% of carbon dioxide gas was introduced by a blow nozzle B into the culture tank so that the concentration of dissolved oxygen in the culture fluid was maintained at 3 ppm by automatic control. The culture fluid in the culture tank was maintained at 37° C. A marine-type stirring vane was attached to the culture tank, and its stirring speed was 60 rpm.

For 4 days after seeding, batchwise culture was performed. As shown in Table 13, the cell density reached $6.1 \times 10^5$/ml on the fourth day after starting the culture. Since this cell density was determined to be the highest density in batchwise culture, and perfusion culture using a centrifugal separator was started. The centrifugal separator charged with the filtrationsterilized culture fluid was driven, and the rotation speed of the centrifugal separator was adjusted so that the centrifuging effect became 80 G. Then, valve X was closed, pump P-II was stopped, and valve Y was opened. In this state, pump P-I was operated to send 200 ml of the culture fluid to the centrifugal separator for 30 minutes at a rate of 6.7 ml/min. The mother liquor separated from the cells in the centrifugal separator was sent to the spent medium vessel AP-3 through line F and stored. In the spent medium vessel AP-3, the cell density was $2.4 \times 10^5$ cells/ml. Immediately after the termination of the foregoing operation, valve X was opened, valve Y was closed and pump P-I was stopped. In this state, pump P-II was operated to send 55 ml of the spent medium to the centrifugal separator at a rate of 11 ml/min. from the vessel AP-3. By this operation, all cells residing in the centrifugal rotor were discharged from the centrifugal separator, and returned to the culture tank AP-1 via the line E. After 55 ml of the spent medium was sent, the pump P-II was stopped. The culturing was continued by performing this operation automatically once every period of time indicated in Table 13. A fresh supply of the culture medium was continuously fed into the culture tank from line A so that the liquid level of the culture tank was constant. On the fifth day after the starting of the culturing and thereafter, the culture fluid containing cells was withdrawn from the culture tank at a rate of 120 ml per day. In the above experiment, $Q/S.\bar{Z}$ was 0.0027 cm/min.; $\theta$ was 30 min., and $\bar{Z}.\theta$ was 2400.

Some of the experimental conditions and the results of the experiment are shown in Table 13.

TABLE 13

| Culturing time (days) | Time interval for feeding to the centrifugal separator (hours) | Number of feedings of the makeup medium per day | Density of living cells (cells/ml) | Concentration of the antibody in the culture fluid (μg/ml) |
|---|---|---|---|---|
| 0 | — | 0 | $1.2 \times 10^5$ | 0 |
| 1 | — | 0 | $1.3 \times 10^5$ | 0.5 |
| 2 | — | 0 | $2.9 \times 10^5$ | 0.9 |
| 3 | — | 0 | $6.1 \times 10^5$ | 2.1 |
| 4 | 2.9 | 1.0 | $1.3 \times 10^6$ | 2.9 |
| 5 | 2.9 | 1.0 | $2.7 \times 10^6$ | 4.6 |
| 6 | 1.9 | 1.5 | $5.5 \times 10^6$ | 5.7 |
| 7 | 1.9 | 1.5 | $9.2 \times 10^6$ | 7.1 |
| 8 | 1.4 | 2.0 | $1.3 \times 10^7$ | 7.3 |
| 9 | 1.4 | 2.0 | $1.4 \times 10^7$ | 9.0 |

EXAMPLE 10

(1) Culture Device

A culture system of the type shown in FIG. 8 was used, the culture tank (AP-1) was a stirred culture tank of glass having a total capacity of 2 liters and designed to receive 1.2 liters as a net volume of a culture fluid.

Into the bottom portion of the culture tank was p t 300 ml of a fluorocarbon (FLUORINERT ® FC-' ®, a product of 3M, U.S.A.) was put.

AP-2 in FIG. 8 was a centrifugal separator equipped with a rotor having a sedimentation area S of 31.4 cm², an effective volume of 11 ml and a rotation radius of 10 cm. Pumps P-I, P-II and P-III were peristaltic pumps.

(2) Culture Medium

A 2:1:1 mixture of RPMI 1640 medium, HAM 12 medium and Dulbecco' modified Eagle medium (to be referred to as RDF) was used as a base medium.

A medium obtained by adding 9 micrograms/ml of insulin, 10 micrograms/ml of transferrin, 10 micrograms/ml of ethanolamine and $2 \times 10^{-6}$ mole/liter of selenous acid to a base medium was used.

(3) Method and Results of Culturing

The culture system was sterilized in advance by autoclaving. Then, 1.2 liters of the culture medium sterilized by filtration was fed into the culture tank, and mouse-human hybridoma × 87 cells obtained by fusing mouse myeloma P3U1 cells and human B cells were seeded so that the cell density became $5 \times 10^5$ cells/ml. These hybridoma cells produce IgG. Oxygen gas containing 5% of carbon dioxide was introduced into the culture tank through a blow nozzle B while the concentration of dissolved oxygen in the culture medium was automatically controlled to 3 ppm. The culture fluid in the culture tank was maintained at 37° C. A marine-type stirring vane was attached to the culture tank, and operated at a stirring speed of 60 rpm.

For 3 days after the seeding, the culturing was carried out batchwise. As shown in Table 14, the cell density reached $1.0 \times 10^6$ cells/ml on the third day after the start of culturing (after the lapse of 24 hours). This density was determined to be the highest in the batchwise culture, and perfusion culture using the centrifugal separator was started. Specifically, the centrifugal separator charged with the filtration-sterilized culture fluid was driven, and the rotation speed of the centrifugal separator was adjusted so that the centrifuging effect became 100 G.

Then, valves X and Z were closed, pumps P-II and P-III were stopped, and valve Y was opened. In this state, pump P-I was operated to send 200 ml of the culture fluid to the centrifugal separator for 10 minutes at a rate of 20 ml/min. The mother liquor separated from the cells in the centrifugal separator was sent to the reservoir tank AP-3 for the spent medium through line F and stored. In the reservoir tank AP-3, the cell density was $5.0 \times 10^4$ cells/ml.

After the foregoing operation was terminated, valve X was opened, valves Y and Z were closed, and pumps P-I and P-III were stopped. In this state, pump P-II was driven to send 50 ml of the perfluorocarbon at the bottom of the culture tank AP-1 at a rate of 5 ml/min. By this operation, all the cells residing in the centrifugal rotor were discharged from the centrifugal separator together with the perfluorocarbon, and returned to the culture tank AP-1 via line E. At the time, the pressure exerted on the cells within the centrifugal rotor was 0.05 kgf/cm$^2$ at the highest.

Thereafter, valve Z was opened, valves X and Y were closed, and pumps P-I and P-II were stopped. In this state, pump P-III was driven to send a fresh supply of the culture medium to the centrifugal separator AP-2 to return the perfluorocarbon in AP-2 to the culture tank AP-1.

The culturing was continued by automatically performing this operation once every period of time shown in Table 14. A fresh supply of the culture medium was fed into the culture tank. In the above experiment, $Q/S.\bar{Z}$ was 0.032 cm/min., $\theta$ was 12.5 min., and $\bar{Z}.\theta$ was 250.

The experimental results are shown in Table 14 together with some of the experimental conditions.

TABLE 14

| Culturing time (days) | Time interval for feeding to the centrifugal separator (hours) | Number of feedings of the makeup medium per day | Density of living cells (cells/ml) | Concentration of the antibody in the culture fluid (μg/ml) |
|---|---|---|---|---|
| 0 | — | 0 | $5 \times 10^5$ | 0 |
| 1 | — | 0 | $6.5 \times 10^5$ | 3 |
| 2 | — | 0 | $1.0 \times 10^6$ | 11 |
| 3 | 4 | 1.0 | $1.6 \times 10^6$ | 9 |
| 4 | 4 | 1.0 | $2.7 \times 10^6$ | 16 |
| 5 | 2.7 | 1.5 | $4.2 \times 10^6$ | 15 |
| 6 | 2.7 | 1.5 | $6.9 \times 10^6$ | 24 |
| 7 | 2 | 2.0 | $9.8 \times 10^6$ | 24 |
| 8 | 2 | 2.0 | $1.1 \times 10^7$ | 31 |
| 9 | 2 | 2.0 | $1.2 \times 10^7$ | 34 |
| 10 | 2 | 2.0 | $1.2 \times 10^7$ | 37 |
| 11 | 2 | 2.0 | $1.3 \times 10^7$ | 39 |

COMPARATIVE EXAMPLE 5

The flow paths in FIG. 8 were changed, and the perfluorocarbon and the fresh medium were fed into the centrifugal rotor from an opening portions located near the rotating axis of the rotor at the time of withdrawing the cells from the centrifugal rotor. The separated cells were withdrawn from an opening portion located remote from the rotating axis of the rotor.

Otherwise, under the same conditions as in Example 10, the mouse-human hybridoma $\times$ 87 cells were cultured.

In the culturing by this method, the pressure exerted on the cells was 0.1 kgf/cm$^2$, and the maximum density of the cells reached decreased by 30% as compared with Example 10. The antibody concentration also decreased by 30%.

By observing the cells taken out from the centrifugal rotor under a microscope, it was seen that the cells were damaged in comparison with the cells withdrawn in Example 10.

EXAMPLE 11

(1) Culture Device

A culture system having a cell separating unit of the type shown in FIG. 9 was used. The culture tank (T1) was a stirred culture tank of glass having a total capacity of 2 liters and designed to receive 1.2 liters as a net volume of the culture medium.

Into the bottom portion of the culture tank, 300 ml of a perfluorocarbon (FLUORINERT® FC-40® a product of 3M, U.S.A.) was put.

The centrifugal separator was one equipped with a rotor having a sedimentation area S of 130 cm$^2$, an effective volume of 75 ml and a rotation radius of 10 cm. Pumps P1, P2 and P3 were peristaltic pumps.

(2) Culture Medium

A 2:1:1 mixture of RPMI 1640 medium, HAM 12 medium and Dulbecco' modified Eagle medium (to be referred to as RDF) was used as a base medium.

A medium obtained by adding 9 micrograms/ml of insulin, 10 micrograms/ml of transferrin, 10 micrograms/ml of ethanolamine and $2 \times 10^{-6}$ mole/liter of selenous acid to a base medium was used.

(3) Method and Results of Culturing

The culture system was sterilized in advance by autoclaving. Then, 1.2 liters of the culture medium sterilized by filtration was fed into the culture tank, and mouse-human hybridoma $\times$ 87 cells obtained by fusing mouse myeloma P3U1 cells and human B cells were seeded so that the cell density became $3.3 \times 10^5$ cells/ml. These hybridoma cells produce IgG. Oxygen gas containing 5% of carbon dioxide was introduced into the culture tank through a blow nozzle B while the concentration of dissolved oxygen in the culture medium was automatically controlled to 3 ppm. The culture fluid in the culture tank was maintained at 37° C. A marine-type stirring vane was attached to the cultivation tank, and operated at a stirring speed of 60 rpm.

For 3 days after the seeding, the culturing was carried out batchwise. As shown in Table 15, the cell density reached $5.8 \times 10^5$ cells/ml on the third day after the start of culturing (after the lapse of 24 hours). This density was determined to be the highest in batchwise culture, and perfusion culture using the centrifugal separator was started. Specifically, the centrifugal separator charged with the filtration-sterilized culture fluid was driven, and the rotation speed of the centrifugal separator was adjusted so that the centrifuging effect became 80 G.

Then, 200 ml of the culture fluid was sent to the centrifugal separator over 10 minutes at a rate of 20 ml/min. The mother liquor separated from the cells by the centrifugal separator flowed into the reservoir tank T2 for the spent culture medium and was stored. The density of the cell therein was $4.0 \times 10^4$ cells/ml.

After the foregoing operation was terminated, pump P-2 was driven to send 120 ml of the perfluorocarbon at the bottom of the culture tank T1 at a rate of 30 ml/min. By this operation, all the cells residing in the centrifugal rotor were discharged from the centrifugal separator together with the perfluorocarbon, and returned to the culture tank T1. At this time, the pressure exerted on the cells within the centrifugal rotor was 0.05 kgf/cm$^2$ at the highest.

Thereafter, pumps P1 and P2 were stopped, and pump P3 was driven to send the fresh medium in T3 to the centrifugal separator S and return the perfluorocarbon in the centrifugal separator to the culture tank T1.

The culturing was continued by automatically performing this operation once every period of time shown in Table 15. A fresh supply of the culture medium was fed continuously into the culture tank so that the liquid level in the culture tank became constant on an average.

The experimental results are shown in Table 14 together with some of the experimental conditions.

TABLE 15

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $3.3 \times 10^5$ | 0 |
| 1 | — | 0 | $4.4 \times 10^5$ | 9 |
| 2 | — | 0 | $5.8 \times 10^5$ | 11 |
| 3 | 4 | 1.0 | $7.6 \times 10^5$ | 15 |
| 4 | 4 | 1.0 | $1.0 \times 10^6$ | 22 |
| 5 | 4 | 1.0 | $1.4 \times 10^6$ | 20 |
| 6 | 4 | 1.0 | $2.1 \times 10^6$ | 21 |
| 7 | 4 | 1.0 | $2.7 \times 10^6$ | 25 |
| 8 | 2 | 2.0 | $3.5 \times 10^6$ | 20 |
| 9 | 2 | 2.0 | $4.5 \times 10^6$ | 29 |
| 10 | 2 | 2.0 | $5.8 \times 10^6$ | 37 |
| 11 | 2 | 2.0 | $7.6 \times 10^6$ | 43 |
| 12 | 2 | 2.0 | $9.8 \times 10^6$ | 49 |
| 13 | 2 | 2.0 | $1.3 \times 10^7$ | 56 |
| 14 | 2 | 2.0 | $1.2 \times 10^7$ | 58 |
| 15 | 2 | 2.0 | $1.4 \times 10^7$ | 61 |
| 16 | 2 | 2.0 | $1.3 \times 10^7$ | 62 |

EXAMPLE 12

(1) Culture Device

A culture system having a cell separating unit of the type shown in FIG. 9 was used. The culture tank T1 was a stirred culture tank of glass having a total capacity of 15 liters and designed to receive 10 liters as a net volume of the culture medium.

Into the bottom portion of the culture tank, 900 ml of a perfluorocarbon (FLUORINERTT ® FC-40 ®, a product of 3M, U.S.A.) was put.

The centrifugal separator was one equipped with a rotor having a sedimentation area S of 130 cm$^2$, an effective volume of 75 ml and a rotation radius of 10 cm, as shown in FIG. 10. Pumps P1, P2 and P3 were peristaltic pumps.

(2) Culture Medium

A 2:1:1 mixture of RPMI 1640 medium, HAM 12 medium and Dulbeccol modified Eagle medium (to be referred to as RDF) was used as a base medium.

A medium obtained by adding 9 micrograms/ml of insulin, 10 micrograms/ml of transferrin, 10 micrograms/ml of ethanolamine and $2 \times 10^{-6}$ mole/liter of selenous acid to a base medium was used.

(3) Method and Results of Culturing

The culture system was sterilized in advance by autoclaving. Then, 10 liters of the culture medium sterilized by filtration was fed into the culture tank, and mouse-human hybridoma×87 cells obtained by fusing mouse myeloma P3U1 cells and human B cells were seeded so that the cell density became $6.2 \times 10^5$ cells/ml. These hybridoma cells produce IgG. Oxygen gas containing 5% of carbon dioxide was introduced into the culture tank through a blow nozzle B while the concentration of dissolved oxygen in the culture medium was automatically controlled to 3 ppm. The culture fluid in the culture tank was maintained at 37° C. A marine-type stirring vane was attached to the cultivation tank, and operated at a stirring speed of 30 rpm.

For 3 days after the seeding, the culturing was carried out batchwise. As shown in Table 16, the cell density reached $9.8 \times 10^5$ cells/ml on the third day after the start of culturing (after the lapse of 24 hours). This density was determined to be the highest in batchwise culture, and perfusion culture using the centrifugal separator was started. Specifically, the centrifugal separator charged with the filtration-sterilized culture fluid was driven, and the rotation speed of the centrifugal separator was adjusted so that the centrifuging effect became 80 G.

Then, 500 ml of the culture fluid was sent to the centrifugal separator over 10 minutes at a rate of 50 ml/min. The mother liquor separated from the cells by the centrifugal separator flowed into the reservoir tank T2 for the spent culture medium and was stored. The density of the cell therein was $1.0 \times 10^4$ cells/ml.

After the foregoing operation was terminated, pump P-2 was driven to send 120 ml of the perfluorocarbon at the bottom of the culture tank T1 at a rate of 30 ml/min. By this operation, all the cells residing in the centrifugal rotor were discharged from the centrifugal separator together with the perfluorocarbon, and returned to the culture tank T1. At this time, the pressure exerted on the cells within the centrifugal rotor was 0.05 kgf/cm$^2$ at the highest.

Thereafter, pumps P1 and P2 were stopped, and pump P3 was driven to send the fresh medium in T3 to the centrifugal separator S and return the perfluorocarbon in the centrifugal separator to the culture tank T1.

The culturing was continued by automatically performing this operation once every period of time shown in Table 16. A fresh supply of the culture medium was fed continuously into the culture tank so that the liquid level in the culture tank became constant on an average.

The experimental results are shown in Table 16 together with some of the experimental conditions.

TABLE 16

| Culturing time (days) | Time interval for feeding to the centrifugal separator (hours) | Number of feedings of the makeup medium per day | Density of living cells (cells/ml) | Concentration of the antibody in the culture fluid (μg/ml) |
| --- | --- | --- | --- | --- |
| 0 | — | 0 | $6.2 \times 10^5$ | 0 |
| 1 | 1.2 | 1.0 | $9.8 \times 10^5$ | 11 |
| 2 | 1.2 | 1.0 | $1.6 \times 10^6$ | 8 |
| 3 | 1.2 | 1.0 | $2.3 \times 10^6$ | 8 |
| 4 | 1.2 | 1.0 | $3.4 \times 10^6$ | 12 |
| 5 | 0.6 | 2.0 | $4.8 \times 10^6$ | 10 |
| 6 | 0.6 | 2.0 | $6.8 \times 10^6$ | 14 |
| 7 | 0.6 | 2.0 | $8.9 \times 10^6$ | 22 |
| 8 | 0.6 | 2.0 | $9.8 \times 10^6$ | 29 |
| 9 | 0.6 | 2.0 | $1.1 \times 10^7$ | 38 |
| 10 | 0.6 | 2.0 | $1.0 \times 10^7$ | 45 |
| 11 | 0.6 | 2.0 | $1.2 \times 10^7$ | 48 |
| 12 | 0.6 | 2.0 | $1.1 \times 10^7$ | 54 |
| 13 | 0.6 | 2.0 | $1.2 \times 10^7$ | 53 |
| 14 | 0.6 | 2.0 | $1.2 \times 10^7$ | 56 |

EXAMPLE 13

(1) Culture Device

A culture system having a cell separating unit of the type shown in FIG. 9 was used. The culture tank T1 was a stirred culture tank of stainless steel having a total capacity of 70 liters and designed to receive 40 liters as a net volume of the culture medium.

Into the bottom portion of the culture tank, 6 l of a perfluorocarbon (FLUORINERTT® FC-40®, a product of 3M, U.S.A.) was put.

The centrifugal separator was one equipped with a rotor having a sedimentation area (S) of 130 cm$^2$, an effective volume (V) of 230 ml and a rotation radius (r) of 13 cm, as shown in FIG. 12. (In FIG. 12, d=0.4 cm and α=75°.) Pumps P1, P2 and P3 were peristaltic pumps.

(2) Culture medium

A 2:1:1 mixture of RPMI 1640 medium, HAM 12 medium and Dulbecco' modified Eagle medium (to be referred to as RDF) was used as a base medium.

A medium obtained by adding 9 micrograms/ml of insulin, 10 micrograms/ml of transferrin, 10 micrograms/ml of ethanolamine and $2 \times 10^{-6}$ mole/liter of selenous acid to a base medium was used.

(3) Method and Results of Culturing

The culture system was sterilized in advance by autoclaving. Then, 40 liters of the culture medium sterilized by filtration was fed into the culture tank, and mouse-human hybridoma×87 cells obtained by fusing mouse myeloma P3U1 cells and human B cells were seeded so that the cell density became $8.1 \times 10^5$ cells/ml. (The maximum density of living cells in the quiescent culture of×87 cells reached $1.1 \times 10^6$ cells/ml.) These hybridoma cells produced IgG. Oxygen gas was introduced into the culture tank through a blow nozzle while the concentration of dissolved oxygen in the culture medium was automatically controlled to 3 ppm. The culture fluid in the culture tank was maintained at 37° C.

A marinetype stirring vane was attached to the cultivation tank, and operated at a stirring speed of 30 rpm.

Perfusion culture using the centrifugal separator was started just after inoculation. Specifically, the centrifugal separator charged with the filtration-sterilized culture fluid was driven, and the rotation speed of the centrifugal separator was adjusted so that the centrifuging effect became 80 G.

Then, 1,500 ml of the culture fluid was sent to the centrifugal separator over 10 minutes at a rate of 150 ml/min. The mother liquor separated from the cells by the centrifugal separator flowed into the reservoir tank T2 for the spent culture medium and was stored. The density of the viable cell therein was about $3 \times 10^4$ cells/ml and the total cell density was $2.5 \times 10^5$ cells/ml.

After the foregoing operation was terminated, pump P-2 was driven to send 300 ml of the perfluorocarbon at the bottom of the culture tank T1 at a rate of 150 ml/min. By this operation, all the cells residing in the centrifugal rotor were discharged from the centrifugal separator together with the perfluorocarbon, and returned to the culture tank T1.

Thereafter, pump P2 was stopped, and pump P3 was driven to send the fresh medium in T3 to the centrifugal separator S and return the perfluorocarbon in the centrifugal separator to the culture tank T1.

The culturing was continued by automatically performing this operation once every period of time shown in Table 17. A fresh supply of the culture medium was fed continuously into the culture tank so that the liquid level in the culture tank became constant on an average.

The experimental results are shown in Table 17 together with some of the experimental conditions. In the above experiment, $\theta = 6$ min.
$\bar{Z} = 8\ 0$.

Therefore, $\bar{Z} \times \theta = 480$ min.
$Q/S.\bar{Z} = 0.0032$ cm/min.

TABLE 17

| Culturing time (days) | Time interval for feeding to the centrifuge (min) | Specific perfusion rate (vol/vol/day) | Viable cell density (cells/ml) | Antibody concentration in the culture fluid (μg/ml) |
| --- | --- | --- | --- | --- |
| 0 | 45 | 1.0 | $8.1 \times 10^5$ | — |
| 1 | 45 | 1.0 | $1.1 \times 10^6$ | — |
| 2 | 45 | 1.0 | $1.7 \times 10^6$ | 9 |
| 3 | 45 | 1.0 | $3.2 \times 10^6$ | 12 |
| 4 | 30 | 1.5 | $4.8 \times 10^6$ | 14 |
| 5 | 30 | 1.5 | $7.8 \times 10^6$ | 35 |
| 6 | 30 | 1.5 | $8.6 \times 10^6$ | 41 |
| 7 | 30 | 1.5 | $9.6 \times 10^6$ | 47 |
| 8 | 30 | 1.5 | $9.8 \times 10^6$ | 53 |
| 9 | 30 | 1.5 | $9.4 \times 10^6$ | 59 |
| 11 | 30 | 1.5 | $9.0 \times 10^6$ | 51 |
| 12 | 30 | 1.5 | $1.1 \times 10^7$ | 57 |
| 14 | 30 | 1.5 | $1.0 \times 10^7$ | 59 |
| 15 | 30 | 1.5 | $8.4 \times 10^6$ | 61 |
| 17 | 30 | 1.5 | $8.6 \times 10^6$ | 56 |
| 18 | 30 | 1.5 | $9.2 \times 10^6$ | 18 |
| 19 | 30 | 1.5 | $1.1 \times 10^7$ | 58 |
| 20 | 30 | 1.5 | $9.6 \times 10^6$ | 60 |
| 21 | 30 | 1.5 | $9.8 \times 10^6$ | 51 |
| 22 | 30 | 1.5 | $9.0 \times 10^6$ | 57 |
| 23 | 30 | 1.5 | $9.4 \times 10^6$ | 55 |

EXAMPLE 14

(1) Culture Device

There was used the same culture device as in Example 13 except a rotor of a centrifugal separator. A rotor with a helical multilayered separation zone having the following characteristics, as shown in FIG. 11, was used as the rotor of the centrifugal separator.

$r = 13$ cm
$\alpha = 60°$
$d = 0.4$ cm
$t = 0.4$ cm
$h = 2.9$ cm
$n^* = 3$
$V = 300$ ml
$S = 590$ cm$^2$

* Number of layers of a sedimentation area (2) Culture Medium

The same culture medium as in Example 13 was used.

(3) Method and Results of Culturing

The culture system was sterilized in advance by autoclaving. Then, 40 liters of the culture medium sterilized by filtration was fed into the culture tank, and mouse-human hybridoma×87 cells were seeded so that the cell density became $2.1 \times 10^5$ cells/ml. These hybrodoma cells produced IgG. Oxygen gas was introduced into the culture tank through a blow nozzle while the concentration of dissolved oxygen in the culture medium was automatically controlled to 3 ppm. The culture fluid in the culture tank was maintained at 37° C.

For 3 days after the seeding, the culturing was carried out batchwise. As shown in Table 18, the cell density reached $6.3 \times 10^5$ cells/ml on the third day after the start of culturing. Perfusion culture using the centrifugal separator was started. Specifically, the centrifugal separator charged with the filtration-sterilized culture fluid was driven, and the rotation speed of the centrifugal separator was adjusted so that the centrifuging effect became 100 G.

Then, 2,000 ml of the culture fluid was sent to the centrifugal separator over 10 minutes at a rate of 200 ml/min. The mother liquor separated from the cells by the centrifugal separator flowed into the reservoir tank T2 for the spent culture medium and was stored. The density of the viable cell therein was about $2 \times 10^4$ cells/ml.

After the foregoing operation was terminated, pump P-2 was driven to send 400 ml of the perfluorocarbon at the bottom of the culture tank T1 at a rate of 200 ml/min. By this operation, all the cells residing in the centrifugal rotor were discharged from the centrifugal separator together with the perfluorocarbon, and returned to the culture tank T1.

Thereafter, pump P2 was stopped, and pump P3 was driven to send the fresh medium in T3 to the centrifugal separator S and return the perfluorocarbon in the centrifugal separator to the culture tank T1.

The culturing was continued by automatically performing this operation once every period of time shown in Table 18. A fresh supply of the culture medium was fed continuously into the culture tank so that the liquid level in the culture tank became constant on an average.

The experimental results are shown in Table 18 together with some of the experimental conditions.

In the above experiment,
$\theta = 6$ min.
$\overline{Z} = 100$.
Therefore,
$\overline{Z} \times \theta = 600$ min.
$Q/S \cdot \overline{Z} = 0.0034$ cm/min.

TABLE 18

| Culturing time (days) | Time interval for feeding to the centrifuge (min) | Specific perfusion rate (vol/vol/day) | Viable cell density (cells/ml) | Antibody concentration in the culture fluid (μg/ml) |
|---|---|---|---|---|
| 0 | — | 0 | $2.1 \times 10^5$ | — |
| 1 | — | 0 | $2.8 \times 10^5$ | — |
| 2 | — | 0 | $5.0 \times 10^5$ | — |
| 3 | — | 1.0 | $6.3 \times 10^5$ | — |
| 6 | 60 | 1.0 | $3.7 \times 10^6$ | 21 |
| 7 | 60 | 1.0 | $4.3 \times 10^6$ | 35 |
| 8 | 60 | 1.0 | $7.2 \times 10^6$ | 48 |
| 9 | 60 | 1.0 | $6.3 \times 10^6$ | 51 |
| 10 | 60 | 1.0 | $7.3 \times 10^6$ | 49 |
| 11 | 60 | 1.0 | $9.0 \times 10^6$ | 61 |
| 13 | 60 | 1.0 | $7.6 \times 10^6$ | 70 |
| 15 | 60 | 1.0 | $8.0 \times 10^6$ | 67 |
| 17 | 60 | 1.0 | $7.3 \times 10^6$ | 72 |
| 20 | 60 | 1.0 | $7.8 \times 10^6$ | 87 |
| 22 | 60 | 1.0 | $7.7 \times 10^6$ | 78 |

EXAMPLE 15

(1) Culture Device

A culture system having a cell separating unit of the type shown in FIG. 13(1) was used. The culture tank T1 was a stirred culture tank of glass having a total capacity of 95 liters and designed to receive 60 liters as a net volume of the culture medium.

Into the bottom portion of the culture tank, 10 l of a perfluorocarbon was put.

A rotor with a concentrically multilayered separation zone, having the following characteristics, as shown in FIG. 13(1), was used as the rotor of the centrifugal separator.

$r = 17$ cm
$\alpha = 45°$
$d = 0.4$ cm
$t = 0.4$ cm
$h = 3$ cm
$n = 2$
$V = 230$ ml
$S = 890$ cm$^2$ (2) Culture Medium A 2:1:1 mixture of RPMI 1640 medium, HAM 12 medium and Dulbeccol modified Eagle medium (to be referred to as RDF) was used as a base medium.

A medium obtained by adding 9 micrograms/ml of insulin, 10 micrograms/ml of transferrin, 10 micrograms/ml of ethanolamine and $2 \times 10^{-6}$ mole/liter of selenous acid to a base medium was used.

(3) Method and Results of Culturing

The culture system was sterilized in advance by autoclaving. Then, 60 liters of the culture medium sterilized by filtration was fed into the culture tank, and mouse-human hybridoma P-8 cells obtained by fusing mouse myeloma P3U1 cells and human B cells were seeded so that the cell density became $1.06 \times 10^6$ cells/ml. (The maximum density of living cells in the quiescent culture of P-8 cells reached $1.3 \times 10^6$ cells/ml.) These hybridoma cells produce IgG. Oxygen gas was introduced into the culture tank through a blow nozzle while the concentration of dissolved oxygen in the culture medium was automatically controlled to 3 ppm. The culture fluid in the culture tank was maintained at 37° C. A marinetype stirring vane was attached to the cultivation tank, and operated at a stirring speed of 30 rpm.

Perfusion culture using the centrifugal separator was started just after inoculation. Specifically, the centrifugal separator charged with the filtration-sterilized culture fluid was driven, and the rotation speed of the centrifugal separator was adjusted so that the centrifuging effect became 120 G.

Then, 2,500 ml of the culture fluid was sent to the centrifugal separator over 10 minutes at a rate of 250 ml/min. The mother liquor separated from the cells by the centrifugal separator flowed into the reservoir tank T2 for the spent culture medium and was stored. The density of the viable cell therein was about $4 \times 10^4$ cells/ml.

After the foregoing operation was terminated, pump P-2 was driven to send 300 ml of the perfluorocarbon at the bottom of the culture tank T1 at a rate of 150 ml/min. By this operation, all the cells residing in the centrifugal rotor were discharged from the centrifugal separator together with the perfluorocarbon, and returned to the culture tank T1.

Thereafter, pump P2 was stopped, and pump P3 was driven to send the fresh medium in T3 to the centrifugal separator S and return the perfluorocarbon in the centrifugal separator to the culture tank T1.

The culturing was continued by automatically performing this operation once every period of time shown in Table 19. A fresh supply of the culture medium was fed continuously into the culture tank so that the liquid level in the culture tank became constant on an average.

The experimental results are shown in Table 19 together with some of the experimental conditions.

In the above experiment,
$\theta = 6$ min.
$\overline{Z} = 120$.
Therefore,
$\overline{Z} \times \theta = 720$ min.
$Q/S.\overline{Z} = 0.0023$ cm/min.

TABLE 19

| Culturing time (days) | Time interval for feeding to the centri-fuge (min) | Specific perfusion rate (vol/vol/day) | Viable cell density (cells/ml) | Antibody concentration in the culture fluid (μg/ml) |
|---|---|---|---|---|
| 0 | 55 | 1.0 | $1.06 \times 10^6$ | — |
| 1 | 55 | 1.0 | $2.7 \times 10^6$ | — |
| 2 | 36 | 1.5 | $4.2 \times 10^6$ | — |
| 3 | 27 | 2.0 | $6.3 \times 10^6$ | — |
| 4 | 27 | 2.0 | $6.8 \times 10^6$ | 37 |
| 5 | 27 | 2.0 | $9.1 \times 10^6$ | 42 |
| 7 | 27 | 2.0 | $1.2 \times 10^7$ | 51 |
| 9 | 27 | 2.0 | $1.7 \times 10^7$ | 65 |
| 11 | 27 | 2.0 | $1.8 \times 10^7$ | 76 |
| 12 | 27 | 2.0 | $1.5 \times 10^7$ | 82 |
| 14 | 27 | 2.0 | $1.8 \times 10^7$ | 83 |
| 16 | 27 | 2.0 | $1.7 \times 10^7$ | 75 |
| 18 | 27 | 2.0 | $1.6 \times 10^7$ | 81 |

What is claimed is:

1. A method of culturing animal cells, which comprises
   (A) subjecting living animal cells to suspension culture in a culture tank,
   (B) withdrawing a portion of the suspension culture fluid containing living animal cells from the culture tank,
   (C) continuously feeding the withdrawn suspension culture fluid into the centrifuging space of a rotating centrifugal separating device for a certain period of time from a feed opening, and continuously withdrawing the mother liquor separated from the living animal cells for a certain period of time from a discharge opening, the centrifugal force acting on the feed opening being higher than that on the discharge opening, and accumulating the living cells in the centrifuging space,
   (D) feeding a liquid medium which is immiscible with water, has a density higher than the animal cells and the culture fluid and does not inhibit the growth of the animal cells into the feed opening while the centrifugal separating device is kept rotating, and withdrawing the living animal cells accumulated in the centrifuging space together with the mother liquor from the discharge opening by pushing them with the liquid medium, and
   (E) returning at least a portion of the withdrawn animal cells to the culture tank for step (A).

2. The method of claim 1 in which steps (B) to (E) are repeatedly carried out.

3. The method of claim 1 in which the centrifugal separating device is operated under the following conditions:

$$\theta \leq 300, \qquad (1)$$

$$\overline{Z} \times \theta \leq 3 \times 10^4 \qquad (2)$$

$$Q/S.\overline{Z} \leq 0.3, \text{ and} \qquad (3)$$

$$5 \leq \overline{Z} \leq 2,000 \qquad (4)$$

wherein
$\theta$ is the average residence time (minutes) of the animal cells in the centrifugal separating device,
$\overline{Z}$ is a centrifuging effect,
Q is the amount (ml/min.) of the suspension culture fluid supplied to the centrifugal separating device per unit time, and
S is the sedimentation area (cm$^2$) when the centrifugal force is acting.

4. A method of culturing animal cells which comprises
   (A) subjecting living animal cells to suspension culture in a culture tank,
   (B) withdrawing a portion of a suspension culture fluid containing the living animal cells from the culture tank,
   (C-1) supplying the withdrawn suspension culture fluid to a centrifugal separating device and separating the living animal cells from the suspension culture fluid, the centrifugal separating device being operated under the following conditions:

$$\theta \leq 300, \qquad (1)$$

$$\overline{Z} \times \theta 3 \times 10^4, \qquad (2)$$

$$Q/S.\overline{Z} \leq 0.3, \text{ and} \qquad (3)$$

$$5 \leq \overline{Z} \leq 2,000 \qquad (4)$$

wherein
$\theta$ is the average residence time (minutes) of the animal cells in the centrifugal separating device,
$\overline{Z}$ is a centrifuging effect,
Q is the amount of the suspension culture fluid supplied to the centrifugal separating device per unit time (ml/min), and
S is the sedimentation area (cm$^2$) when the centrifugal force is acting, (C-2) separating the animal cells from the suspension culture fluid in the centrifugal separating device in the presence of a liquid carrier which
(a) is substantially immiscible with water,
(b) has a higher density than water and the cells which are to be separated from the suspension, and
(c) does not substantially inhibit the growth of the animal cells,
(b) withdrawing the separated living animal cells from the centrifugal separating device, and
(E) recycling at least a portion of the withdrawn living animal cells to the culture tank for step (A).

5. The method of claim 4 wherein the animal cells are hybrodoma cells.

6. The method of claim 4 wherein a serum-free culture medium is used for the suspension culture.

7. The method of claim 4 wherein the withdrawal of a portion of the suspension culture fluid in step (B) is carried out through a conduit extending from the culture tank.

8. The method of claim 4 wherein the centrifugal separating device is provided with
(a) an opening for feeding a suspension culture medium,
(b) a sedimentation surface having such a structure that the sedimented animal cells can move along the sedimentation surface,
(c) an animal cell gathering portion where the animal cells which have moved along the sedimentation surface gather,
(d) an opening for withdrawing the animal cells from the animal cell gathering portion and
(e) a mother liquor discharge opening for discharging the mother liquor of the culture from which the animal cells have been separated.

9. The method of claim 4 wherein the centrifugal separating device is operated under conditions that provide an average animal cell residence time ($\theta$) of not more than 150 minutes.

10. The method of claim 4 wherein the centrifugal separating device is operated with a centrifugal effect ($\bar{Z}$) of 10 to 1,000.

11. The method of claim 4 wherein the centrifugal separating device is operated under the following condition:

12. The method of claim 4 wherein the centrifugal separating device is operated under the following condition:

$$Q/S.\bar{Z} \leq 0.2,$$

13. The method of claim 4 wherein the centrifugal separating device is operated under the following operating conditions:

$$\theta \leq 150, \quad (1)$$

$$\bar{Z} \times \theta \leq 2 \times 10^4, \quad (2)$$

$$Q/S.\bar{Z} \leq 0.2, \text{ and} \quad (3)$$

$$10 \leq \bar{Z} \leq 1,000 \quad (4)$$

14. The method of claim 4 wherein the centrifugal separating device is operated under the following operating conditions:

$$\theta \leq 60, \quad (1)$$

$$\bar{Z} \times \theta \leq 2 \times 10^4, \quad (2)$$

$$Q/S.\bar{Z} \leq 0.1, \text{ and} \quad (3)$$

$$20 \leq \bar{Z} \leq 300. \quad (4)$$

15. The method of claim 4 wherein the liquid carrier is a perfluorocarbon.

16. A method of separating animal cells and an aqueous solution from a living animal cell-containing aqueous suspension of cells which comprises
(A-1) providing a rotating centrifugal separator, including a central rotor in which
(i) there exists a centrifugal space which consists of a peripheral slot having an outside peripheral wall
(ii) the peripheral slot has an outside wall with a length corresponding to an angular range of not less than 360° around the central axis of the rotor,
(iii) the peripheral slot has a space such that liquid forms a continuous flow,
(iv) the peripheral slot has a feed or discharge opening for the liquid at, or near, the furthest position from the central axis of the rotor, and
(v) the peripheral slot has a feed or discharge opening for the liquid at, or near, the nearest position from the central axis of the rotor,
(A-2) feeding a living animal cell-containing aqueous suspension to the feed or discharge opening for the liquid fluid in (iv) in the rotating centrifugal separator, while withdrawing the aqueous solution separated from the living animal cells via the feed or discharge opening for the liquid fluid in (v), and accumulating the animal cells in the space of the centrifugal separator,
(B) then feeding a liquid carrier, which is immiscible with water, has a higher density than the animal cells and the aqueous solution and does not inhibit the growth of the animal cells, to the feed or discharge opening for the liquid in (iv) in the rotating centrifugal separator and then withdrawing the living animal cells together with the remaining aqueous solution by pushing them out with the liquid carrier from the feed or discharge opening for the liquid fluid in (v) to thereby obtain the living animal cells, and
(C) further feeding a fresh or spend medium solution to the feed or discharge for the liquid fluid in (v) in the rotating centrifugal separator, and withdrawing the liquid carrier from the feed or discharge opening the liquid fluid in (iv) to separate the liquid carrier.

17. The method of claim 16 wherein the liquid carrier is a fluorocarbon.

18. The method of any one of claims 16 or 17 wherein the centrifugal separator is operated under the following conditions:

$$\theta \leq 300, \quad (1)$$

$$\bar{Z} \times \theta \leq 3 \times 10^4, \quad (2)$$

$$Q/S.\bar{Z} \leq 0.3, \text{ and} \quad (3)$$

$$S \leq \bar{Z} \leq 2,000 \quad (4)$$

wherein

θ is an average residence time (minutes) of the animal cells int he centrifugal separating device,
$\bar{Z}$ is a centrifuging effect,
Q is the amount of the suspension culture fluid supplied to the centrifugal separating per unit time (ml/min), and
S is the sedimentation area (cm$^2$) when the centrifugal force is acting.

19. A method of culturing animal cells in suspension, which comprises,
   (a) culturing living animal cells in suspension in a culture tank,
   (b) withdrawing a portion of the living animal cell-containing suspension culture fluid from the culture tank,
   (c) feeding the withdrawn suspension culture fluid to a rotating centrifugal separator having a central rotor in which
      (i) there exists a centrifugal space which consists of a peripheral slot having an outside peripheral wall having an inclination angle, the inclination angle being defined as the angle between the slot surface and the centrifugal direction, said angle being between 30° and 80°,
      (ii) the peripheral slot has an outside wall with a length corresponding to an angular range of not less than 360° around the central axis of the rotor,
      (iii) the peripheral slot has a space such that the liquid from said suspension forms a continuous flow,
      (iv) the peripheral slot has a feed or discharge opening for the liquid at, or near, the furthest position from the central axis of the rotor, and
      (v) the peripheral slot has a feed or discharge opening for the liquid at, or near, the nearest position from the central axis or the rotor,
   at the feed or discharge opening in (iv) for a certain period of time, while withdrawing the culture fluid separated from the living cells via the feed or discharge opening for the liquid in (v), and accumulating the animal cells within the space of the centrifugal separator,
   (d) then feeding a liquid carrier which is immiscible with water, has a higher density than the animal cells and the culture fluid and does not inhibit the growth of the animal cells to the feed or discharge opening for the liquid in (iv) in the centrifugal separator, and withdrawing the living animal cells by pushing them out together with the culture fluid from the feed or discharge opening for the liquid in (v),
   (e) returning at least a portion of the withdrawn animal cells to the culture tank for step (a), and
   (f) further feeding a fresh culture fluid or the culture fluid withdrawn in step (c) from the feed or discharge opening for the liquid in (v) in the centrifugal separator, and withdrawing the liquid carrier from the feed or discharge opening for the liquid in (iv) to recover the liquid carrier from the discharge opening for the liquid in (iv).

20. The method of claim 19 wherein steps (b) to (f) are repeated.
21. The method of claim 19 or 20 wherein the animal cells are hybridoma cells.
22. The method of any one of claims 19 or 20 wherein the liquid carrier is a fluorocarbon.
23. The method of any one of claims 19 or 20 wherein the centrifugal separator is operated under the following conditions:

$$\theta \leq 300, \quad (1)$$

$$\bar{Z} \times \theta \leq 3 \times 10^4, \quad (2)$$

$$Q/S.\bar{Z} \leq 0.3, \text{ and} \quad (3)$$

$$S \leq \bar{Z} \leq 2,000 \quad (4)$$

wherein
θ is an average residence time (minutes) of the animal cells in the centrifugal separator,
$\bar{Z}$ is a centrifuging effect,
Q is the amount of the suspension culture fluid supplied to the centrifugal separator per unit time (ml/min), and
S is the sedimentation area (cm$^2$) when the centrifugal force is acting.

24. The method of claim 21 wherein the liquid carrier is a fluorocarbon.
25. The method of claim 21 wherein the centrifugal separator is operated under the following conditions:

$$\theta \leq 300, \quad (1)$$

$$\bar{Z} \times \theta \leq 3 \times 10^4, \quad (2)$$

$$Q/S.\bar{Z} 0.3, \text{ and} \quad (3)$$

$$S \leq \bar{Z} \leq 2,000 \quad (4)$$

wherein
θ is an average residence time (minutes) of the animal cells in the centrifugal separator,
$\bar{Z}$ is a centrifuging effect,
Q is the amount of the suspension culture fluid supplied to the centrifugal separator per unit time (ml/min), and
S is the sedimentation area (cm$^2$) when the centrifugal force is acting.

26. The method of claim 22 wherein the centrifugal separator is operated under the following conditions:

$$\theta \leq 300, \quad (1)$$

$$\bar{Z} \times \theta \leq 3 \times 10^4, \quad (2)$$

$$Q/S.\bar{Z} \leq 0.3, \text{ and} \quad (3)$$

$$S \leq \bar{Z} \leq 2,000 \quad (4)$$

wherein
θ is an average residence time (minutes) of the animal cells in the centrifugal separator,
$\bar{Z}$ is a centrifuging effect,
Q is the amount of the suspension culture fluid supplied to the centrifugal separator per unit time (ml/min), and
S is the sedimentation area (cm$^2$) when the centrifugal force is acting.

27. The method of claim 24 wherein the centrifugal separator is operated under the following conditions:

$$\theta \leq 300, \quad (1)$$

$$\bar{Z} \times \theta \leq 3 \times 10^4, \quad (2)$$

$$Q/S.\bar{Z} \leq 0.3, \text{ and} \quad (3)$$

$$S \leq \overline{Z} 2{,}000 \qquad (4)$$

wherein
  $\theta$ is an average residence time (minutes) of the animal cells in the centrifugal separator,
  $\overline{Z}$ is a centrifuging effect,
  Q is the amount of the suspension culture fluid supplied to the centrifugal separator per unit time (ml/min), and
  S is the sedimentation area (cm$^2$) when the centrifugal force is acting.

* * * * *

UNITED STATES PATENT AND TRADEMARK OFFICE
CERTIFICATE OF CORRECTION

PATENT NO. 5,250,432

DATED : October 5, 1993

INVENTOR(S) : Michiyuki TOKASHIKI et al.

It is certified that error appears in the above-indentified patent and that said Letters Patent is hereby corrected as shown below:

On title page, item [19] change "Takashiki et al" to --Tokashiki et al--
On title page, item [75] change the last name of the first inventor from "Takashiki" to --Tokashiki--.

Signed and Sealed this

Third Day of May, 1994

Attest:

BRUCE LEHMAN

Attesting Officer

Commissioner of Patents and Trademarks